US009615847B2

(12) United States Patent
Kirkemo et al.

(10) Patent No.: US 9,615,847 B2
(45) Date of Patent: Apr. 11, 2017

(54) DEVICES AND METHODS FOR SOFT TISSUE HYDRO DISSECTION

(71) Applicant: Boston Scientific Scimed, Inc., Maple Grove, MN (US)

(72) Inventors: Aaron Kirkemo, Gladstone, NJ (US); Jamie Li, Lexington, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 98 days.

(21) Appl. No.: 14/547,753

(22) Filed: Nov. 19, 2014

(65) Prior Publication Data

US 2015/0142039 A1    May 21, 2015

Related U.S. Application Data

(60) Provisional application No. 61/907,140, filed on Nov. 21, 2013.

(51) Int. Cl.
| | |
|---|---|
| *A61B 17/00* | (2006.01) |
| *A61B 17/3203* | (2006.01) |
| *A61B 17/34* | (2006.01) |
| *A61B 17/42* | (2006.01) |
| *A61B 1/00* | (2006.01) |

(Continued)

(52) U.S. Cl.
CPC ........ *A61B 17/3203* (2013.01); *A61B 1/0014* (2013.01); *A61B 1/018* (2013.01); *A61B 1/32* (2013.01); *A61B 17/3417* (2013.01); *A61B 17/3478* (2013.01); *A61B 17/42* (2013.01); *A61B 1/303* (2013.01); *A61B 1/31* (2013.01); *A61B 2017/00805* (2013.01); *A61B 2017/320044* (2013.01);

(Continued)

(58) Field of Classification Search
CPC .... A61F 2009/0087; A61F 2009/00887; A61F 9/00754; A61B 17/00234; A61B 2017/00805; A61B 17/06109; A61B 17/3203; A61B 17/42; A61B 2017/320044
USPC ................ 606/107, 159, 167, 170, 185, 190
See application file for complete search history.

(56) References Cited

U.S. PATENT DOCUMENTS

| | | | |
|---|---|---|---|
| 3,320,948 | A | 5/1967 | Martin |
| 4,585,438 | A | 4/1986 | Makler |

(Continued)

FOREIGN PATENT DOCUMENTS

| | | |
|---|---|---|
| WO | 2009157927 A1 | 12/2009 |
| WO | 2013022957 A1 | 2/2013 |
| WO | 2015077465 A1 | 5/2015 |

OTHER PUBLICATIONS

Final Office Action for U.S. Appl. No. 13/568,848, mailed on Oct. 13, 2016, 11 pages.

(Continued)

*Primary Examiner* — Katherine M Shi
(74) *Attorney, Agent, or Firm* — Brake Hughes Bellermann LLP

(57) ABSTRACT

In one embodiment, a medical device may include an insertion member configured to be inserted into a body opening, and a needle member, movably coupled to the insertion member, configured to be inserted into the body opening. The needle member may include a lumen configured to transfer dissection fluid, a blunt tip located on a distal end of the needle member, and an opening disposed proximate to the blunt tip that is configured to discharge the dissection fluid into a space between tissue layers.

18 Claims, 14 Drawing Sheets

(51) Int. Cl.
*A61B 1/018* (2006.01)
*A61B 1/32* (2006.01)
A61B 17/32 (2006.01)
A61B 1/303 (2006.01)
A61B 1/31 (2006.01)
A61B 90/00 (2016.01)

(52) U.S. Cl.
CPC ............... *A61B 2017/3405* (2013.01); *A61B 2017/3456* (2013.01); *A61B 2090/065* (2016.02)

(56) References Cited

U.S. PATENT DOCUMENTS

| | | | | |
|---|---|---|---|---|
| 5,254,106 | A | * | 10/1993 | Feaster ............... A61F 9/00736 604/272 |
| 5,380,292 | A | | 1/1995 | Wilson |
| 5,499,964 | A | | 3/1996 | Beck |
| 5,628,734 | A | | 5/1997 | Hatfalvi |
| 5,897,590 | A | | 4/1999 | Donovan |
| 6,293,952 | B1 | * | 9/2001 | Brosens ............ A61B 17/00234 604/164.01 |
| 6,565,590 | B2 | | 5/2003 | Kieturakis |
| 7,862,542 | B1 | | 1/2011 | Harmon, Sr. |
| 2001/0047151 | A1 | | 11/2001 | Xian |
| 2004/0106846 | A1 | | 6/2004 | Gellman |
| 2006/0155169 | A1 | | 7/2006 | Bastia |
| 2008/0009895 | A1 | | 1/2008 | Pokomey |
| 2008/0091188 | A1 | | 4/2008 | Gade |
| 2010/0217151 | A1 | | 8/2010 | Gostout |
| 2011/0105850 | A1 | | 5/2011 | Voegele |
| 2011/0218444 | A1 | | 9/2011 | Steffen |
| 2011/0230833 | A1 | | 9/2011 | Landman |
| 2011/0264125 | A1 | * | 10/2011 | Wilson ................... A61B 90/02 606/159 |
| 2012/0130282 | A1 | | 5/2012 | Galloway |
| 2013/0041232 | A1 | | 2/2013 | Li |
| 2015/0094532 | A1 | * | 4/2015 | Wilson ............... A61B 1/00082 600/104 |

OTHER PUBLICATIONS

Final Office Action Response for U.S. Appl. No. 13/568,848, filed Mar. 17, 2016, 7 pages.
Non Final Office Action for U.S. Appl. No. 13/568,848, mailed on Jun. 22, 2016, 12 pages.
Response to Non Final Office Action for U.S. Appl. No. 13/568,848, filed Sep. 20, 2016, 7 pages.
International Application Serial No. PCT/US2012/049975, Invitation to Pay Additional Fees mailed Nov. 14, 2012, 7 pages.
International Application Serial No. PCT/US2012/049975, Search Report and Written Opinion mailed Jan. 10, 2013, 22 pages.
International Application Serial No. PCT/USUS12/49975, International Preliminary Report on Patentability mailed Feb. 20, 2014, 9 Pages.
Final Office Action for U.S. Appl. No. 13/568,848, mailed Jan. 21, 2016, 15 Pages.
Non-Final Office Action for U.S. Appl. No. 13/568,848, mailed Sep. 2, 2015, 11 pages.
Response to Non-Final Office Action for U.S. Appl. No. 13/568,848, filed on Nov. 25, 2015, 8 pages.
Response to Restriction Requirement for U.S. Appl. No. 13/568,848, mailed on Aug. 24, 2015, 1 page.
Restriction Requirement for U.S. Appl. No. 13/568,848, mailed Jun. 25, 2015, 7 Pages.
International Search Report and Written Opinion for PCT Application No. PCT/US14/66642, mailed May 12, 2015, 18 pages.
Invitation to Pay Add'l Fees and Partial Search Report for PCT Application No. PCT/US14/66642, mailed Mar. 17, 2015, 6 pages.
Riley, et al., "The Episure Syringe: A Novel Loss of Resistance Syringe for Locating the Epidural Space", International Anesthesia Research Society, Anesthesia & Analgesia, Brief Report, vol. 105, No. 4, Oct. 2007, pp. 1164-1166.

* cited by examiner

DEVICES AND METHODS FOR SOFT TISSUE HYDRO DISSECTION

CROSS-REFERENCE TO RELATED APPLICATION

This application is a Nonprovisional of, and claims priority to, U.S. Patent Application No. 61/907,140, filed on Nov. 21, 2013, entitled "DEVICES AND METHODS FOR SOFT TISSUE HYDRO DISSECTION", the disclosure of which is incorporated by reference herein in its entirety.

TECHNICAL FIELD

This disclosure relates generally to medical devices and surgical procedures, and particularly medical devices and methods used for preparing a patient's body to receive a bodily implant.

BACKGROUND

Mesh erosion can be a side effect after mesh repair, especially for female pelvic prolapse. Mesh, for example of an implant, erodes out of the tissues where mesh is originally implanted and thus, prevents curing/healing of the tissues. One cause of mesh erosion may be that the tissue layer for mesh placement is incorrect or is not properly prepared.

In some procedures, an operator dissects the tissue layer and creates a pocket or space for placing the mesh, for example, in between the vagina and the bladder. The pocket/space may be required because there may not be space for mesh placement in a normal tissue. The operator may identify a position and make an incision of about 2-3 cm in length inside the vagina. Then the operator may insert a finger to find a way through the incision and may continue dissecting it till the appropriate layer is located for creating the pocket. In this manner, the operator may get a hypothetical idea about the layer to be dissected for creating the pocket. In such cases, dissecting the tissue layer too close to the vagina sides can cause mesh erosion through the vagina after placement of the mesh. Typically, identification of the erosion may happen when a patient starts facing problems after one to three months of the mesh implant, for example. Also, dissection of the tissue layer at a deeper location may result in damage or perforation to the bladder. Therefore, it may be important for an operator to dissect at a proper depth for the prevention of the erosion and damage to the bladder.

In both the cases of close and deep dissection, the operator may rely on his hypothesis and experience to identify the depth of the tissue layer for dissection. However, if the operator cannot identify a fixed location within the tissue layer confidently, it may result in mesh erosion some time after its placement.

In light of the above, there may be a need for a medical device and a method that may assist the operator to conduct dissection at a desired depth. Thus, a medical device and a procedure that controls the depth of insertion to the desired depth inside the tissue layer may be required.

SUMMARY

In one embodiment, a medical device may include an insertion member configured to be inserted into a body opening, and a needle member, movably coupled to the insertion member, configured to be inserted into the body opening. The needle member may include a lumen configured to transfer dissection fluid, a blunt tip located on a distal end of the needle member, and an opening disposed proximate to the blunt tip that is configured to discharge the dissection fluid into a space between tissue layers.

In one embodiment, the medical device may include an injection assembly. The injection assembly may include a needle member having a blunt tip and an opening disposed proximate to the blunt tip, a first receptacle configured to store fluid, and a second receptacle configured to store fluid, where the second receptacle may store a different amount of fluid than the first receptacle. The injection assembly may also include a pressure sensor configured to sense a tissue pressure when the blunt tip is inserted into one or more tissue layers of a body, and an injection member configured to inject the fluid from the first receptacle into a space when the tissue pressure drops below a predetermined pressure level, where the second receptacle is configured to inject the fluid into the space after the fluid from the first receptacle has been injected.

In one embodiment, a method may include inserting a medical device into an opening of the body, where the medical device may include a needle member, a receptacle storing dissection fluid, and an opening disposed proximate to the needle member. The method may further include inserting the needle member into one or more tissue layers of the body until reaching a space, and injecting a dissection fluid from the receptacle to the space via the opening of the needle member.

DETAILED DESCRIPTION

Figure 1:
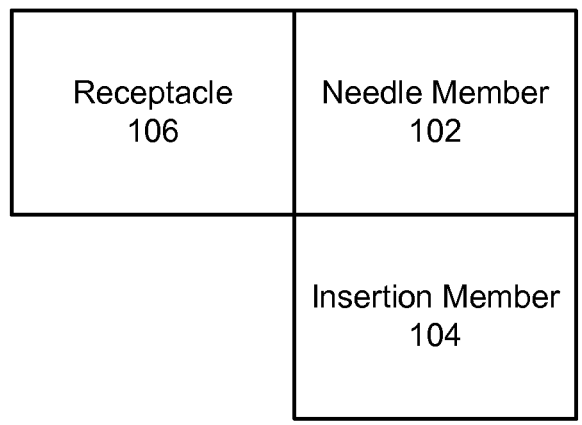
FIG. 1 is a schematic diagram of a medical device configured to create a space between tissue layers in the body of a patient.

Detailed embodiments are disclosed herein. However, it is understood that the disclosed embodiments are merely examples, which may be embodied in various forms. Therefore, specific structural and functional details disclosed herein are not to be interpreted as limiting, but merely as a basis for the claims and as a representative basis for teaching one skilled in the art to variously employ the embodiments in virtually any appropriately detailed structure. Further, the terms and phrases used herein are not intended to be limiting, but to provide an understandable description of the invention.

The terms "a" or "an," as used herein, are defined as one or more than one. The term "another," as used herein, is defined as at least a second or more. The terms "including" and/or "having", as used herein, are defined as comprising (i.e., open transition). The term "coupled" or "moveably coupled," as used herein, is defined as connected, although not necessarily directly and mechanically.

In general, the embodiments are directed to systems, methods, and devices for locating and hydro-dissecting any space for various types of procedures such as treating female pelvic prolapse, or anal prolapse in males or females, for example. Also, the systems, methods, and devices described herein may be used for transabdominal and transvaginal dissection, and graft placement (e.g., mesh or biologic graft), as well as dissecting the suburethral plane for sling placement. More generally, the systems, methods, and devices of the embodiments may be used for any procedure for creating a space such as the Vesico-Vaginal-Septum (VVS), the Recto-Vaginal-Septum (RVS), or the pleural space, among others. In another example, the systems, methods, and devices of the embodiments may be used in the dissection of the prostate during Holmium Laser Ablation of the Prostate (HOLAP). Further, the injection devices and methods may involve injecting intrathecal antibiotics, steroids, sclerosing agents, and/or any type of fluid, for example. As described below in various illustrative embodiments, the embodiments provide systems, methods, and devices employing an improved needle number and/or insertion member configured to adjust and/or control the depth of insertion of a surgical needle within one or more tissue layers of a patient and/or an improved injection member configured to control the injection of dissection fluids into an area within the body of the patient for hydro-dissection of a tissue layer and/or an improved injection member that helps facilitate a more timely or quicker dissection of tissue. One or more of these embodiments may be based on a loss of resistance technique.

The term patient may hereafter be used for a person who benefits from the medical device or the methods disclosed in the present application. For example, the patient can be a person whose body is operated through the medical device or the method disclosed by the present invention. For example, in some embodiments, the patient may be a human female, a human male, or any other mammal.

The terms proximal and distal described in relation to various devices, apparatuses, and components as discussed in the subsequent text of the present application are referred with a point of reference. The point of reference, as used in this description, is a perspective of an operator. The operator may be a surgeon, a physician, a nurse, a doctor, a technician, and the like who may perform the procedure and operate the medical device as described in the present invention. The term proximal refers to an area or portion that is closer or closest to the operator during a surgical procedure. The term distal refers to an area or portion that is farther or farthest from the operator.

FIG. 1 is a schematic diagram of a medical device 100 configured to prepare a patient's body for receiving a bodily implant (not shown), and/or open a space for any of the procedures described herein. Further, the medical device 100 of FIG. 1 (or any of the other figures) may be used in other application areas such as mouth, throat, and/or esophagus. The bodily implant can be a mesh-based device (e.g., a sling), used in the treatment of fecal incontinence, urinary incontinence, prolapse, and other such disorders. In one example, the medical device 100 may be used for opening up spaces between tissues layers before receiving the bodily implant or before starting the dissection for a sacrocolpopexy. The medical device 100 may include a needle member 102, an insertion member 104, and a receptacle 106.

The needle member 102 may be movably coupled to the insertion member 104 and configured to be inserted into one or more tissue layers. The needle member 102 may have a proximal end portion and a distal end portion. In some examples, the needle member 102 may include one or more opening (or ports), and the distal end portion and the one or more openings may assist in the dissection, as further described below. In some examples, the needle member 102 may have a tip that has a shape or structure which assists in the dissection of tissue layers. In some examples, the distal end portion of the needle member 102 may have a blunt tip. The blunt tip may be a non-sharp tip (or semi-sharp tip). The blunt tip may be rounded or relatively smooth. The blunt tip may have a structure that is configured to pierce through some tissue materials but relatively difficult to pierce through other tissue materials. In one example, if the blunt tip is inserted into one side of a vagina wall, the blunt tip may be configured to pierce tissue layers such as the vaginal mucosa, vaginal muscle, and paravaginal fascia in order to reach the Vesico Vaginal Space (VVS), but not easily pierce the deeper tissue layers such as the paravesical fascia, bladder muscle, and bladder muscosa. If the blunt tip is inserted into the other side of the vagina wall, the blunt tip may be configured to pierce tissue layers such as the vaginal mucosa, the vaginal muscle, and the paravaginal fascia to reach the Recto Vaginal Space (RVS), but not easily pierce the deeper tissues layers such as the paravesical fascia, the rectal muscle, and the rectal muscosa. In this manner, the depth of insertion may be controlled based on the structure of the needle member 102.

It is noted that the term space may refer to any area between tissue layers. For example, before the operator makes an incision into tissue layers in a body opening or inserting a medical implant, the operator may want to separate some tissue layers from another other tissue layers, thereby creating a space. The space may be created in order to fit a mesh implant and/or separate tissue layers which should not be pierced. In one example, the operator may insert the needle member 102 in the body opening through one or more tissue layers until reaching the space, and then injecting dissection fluid through the needle member into the space in order to create an actual space. This process may be referred to hydrodissection. In one example, the space may be the VVS and/or the RVS. However, the embodiments encompass any types of possible areas between tissue layers.

The needle member 102 may include a lumen configured to transfer dissection fluid from the receptacle 106 storing the dissection fluid, and one or more openings (also can be referred to as ports) located on the distal end portion of the needle member 102, e.g., proximate to the blunt tip. In one example, the needle member 102 may include multiple openings located proximate to the distal end portion of the needle member 102. For example, the lumen may extend from a proximate end of the needle member 102 to the opening located proximate to the blunt tip, e.g., a distal end of the needle member 102. As such, when the needle member 102 is positioned to its desired depth, the opening is configured to discharge the dissection fluid from the lumen into the desired location such as the VVS or the RVS. In one example, the opening may be considered a port. The port may be a side port, or a port located on at least a portion of the side of the needle member 102. In some examples, the needle member 102 may have multiple ports. In one example, the side port may be disposed on a side wall of the needle member 102. The side port may be disposed on a distal end portion of the needle member 102, and the side port may be proximate to the blunt tip. In a further example, the side portion may be disposed at an angle with respect to a longitudinal axis of the needle member 102. In some examples, the ports and/or the needle member 102 may be shaped to operate as nozzle(s) to improve infusion and dissection. In this context, hydrodissection may refer to opening up the space (e.g., the VVS and/or the RVS) before making a vaginal incision. Usually 40 to 100 cc or more of dissection fluid will be injected into each of the spaces. This opens up the space so the incision can be extended along the paravaginal fascia without disturbing the deeper fascial planes. In some examples, the needle member 102 may be rotated to allow dissection fluid to be directed at different angles or layers.

In one example, the needle member 102 may be bent at a distal end portion of the needle member 102, and rather than having a tapered sharp point, the blunt tip may be considered to have an ovoid tip defining a bevel having a rounded convex edge. In some examples, the needle member 102 may have a curvilinear bevel. Proximate to the bevel, the needle member 102 may define the opening to transfer the dissection fluid to its desired location. In one example, the needle member 102 may be a Tuohy needle or a Tuohy-based needle. Conventionally, the Tuohy needle is designed for performing epidural anesthetic injections. However, according to the embodiments, the Tuohy needle may be utilized as the needle member 102 for preparing the patient's body for an implant such as vaginal/anal hydrodissection. In another example, one of or more features of the Tuohy needle may be modified such as modifying the sharpness of the blunt tip, the location of the opening, or generally, the overall structure of the Tuohy needle itself. In some examples, the needle member 102 may be pre-bent. In some examples, the needle member 102 may be bendable to allow the needle member 102 to align with tissue layers.

In one example, the needle member 102 may be inserted into the body such that the operator may feel a loss of resistance when the blunt tip penetrates a certain tissue layer (e.g., the paravaginal fascia) (thereby reaching its desired location), which, if inserted further into the body, the blunt tip may push the deeper tissues away (as opposed to piercing them), thereby reducing the risk of the needle member 102 of entering unwanted tissue areas. In this manner, the depth of insertion may be controlled based on the structure of the needle member 102.

Using a conventional sharp point needle to perform the hydrodissection requires great skill. If performed incorrectly, the vaginal muscle and mucosa may be pierced. If, in the course of this, the operator does not reach the paravaginal space (i.e. the VVS or RVS), it can result in the operator creating an artificial seroma in the vaginal wall and then erroneously developing a tissue plane within the vaginal wall. Similarly, if the needle tip reaches an area beyond its desired location, a dissection of the wall of the bladder or the rectum may occur.

The receptacle 106 may be configured to store dissection fluid, as well as any other type of fluid used for preparing a patient's body for receiving an implant. The receptacle 106 may be coupled to the needle member 102. In one example, the receptacle 106 may be directly coupled to the needle member 102. In other examples, the receptacle 106 may be indirectly coupled to the needle member 102 via connection lines or other immediate components.

The receptacle 106 maybe any type of reservoir capable of housing the dissection fluid. In some examples, the receptacle 106 may be a syringe, distensible bladder, chamber, or generally any type of housing capable of housing the pressurized dissection fluid. The receptacle 106 may have a structure that is fixed (e.g., like a syringe), or have a structure that is expandable. Also, the size of the receptacle 106 may vary. In one embodiment, the size of the receptacle 106 may be designed such that the dissection fluid may be injected into the space to fully develop the VVS and/or the RVS without replacing the receptacle 106 with another receptacle 106. For example, smaller-type syringes may typically hold 5 cc of fluid. Larger-type syringes may typically hold 20 or 30 cc of fluid. However, the volume of fluid used for vaginal hydrodissection may be over 100 cc of fluid. As such, for smaller-type syringes and larger-type syringes, syringe exchanges may be required to develop the appropriate amount of fluid to fully develop the space. However, the needle member 102 in a 3-5 mm thick vaginal wall can easily slip out of place during syringe exchanges. Therefore, in one embodiment, the receptacle 106 may be configured to hold 100 cc to 200 cc of dissection fluid in order to avoid syringe exchanges. In some examples, the receptacle 106 may have components (e.g., button and/or values) that allow a user to control the dissection.

In one example, the receptacle 106 maybe a pressurized reservoir of dissection fluid. In this example, the receptacle 106 may be a fluid chamber having pressurized dissection fluid. In some examples, the dissection fluid may be pressurized, and the dissection fluid may be released from the fluid chamber to the space via the opening of the needle member 102.

In another example, the receptacle 106 may be a loss of resistance (LOR) receptacle such as a syringe, for example. In one example, the LOR receptacle may be a spring-loaded device. For example, the LOR receptacle 106 may include a compression spring, barrel, and plunger. In this example, the dissection fluid drawn up into the receptacle 106 may empty only when the needle member 102 enters a space with a relatively low tissue pressure, e.g., less than the spring constant associated with the compression spring. In this manner, the dissection fluid is automatically discharged from the LOR receptacle 106 when the LOR receptacle 106 senses that the tissue pressure is lower than the spring constant.

Also, the receptacle 106 may include multiple reservoirs of dissection fluid (e.g., two or more). The multiple reservoirs of dissection fluid may include non-pressurized receptacles, pressurized receptacles, LOR receptacles, and/or any combination thereof. In some examples, a first receptacle may enclose dissection fluid used for a single application of dissection fluid (e.g., 5 cc), and a second receptacle may enclose the remaining dissection fluid (e.g., 95 cc or more). In this example, the first receptacle may be a device configured to sense the tissue pressure such as a LOR syringe that holds a relatively small amount of dissection fluid. As the needle member 102 enters the space, the tissue pressure may drop which causes the first receptacle to release the dissection fluid into the space. At this time, the operator may know that the needle member 102 has entered the correct location because the dissection fluid from the first receptacle is starting to empty out of the first receptacle. Then, the operator may activate the second receptacle (which stores a larger amount of fluid) to inject additional fluid into the space to fully develop it. In this manner, an exchange of receptacles or syringes may be avoided.

In some embodiments, the needle member 102 may be part of another assembly such as an injection assembly. The injection assembly may include at least a portion of the needle member 102. Also, the injection assembly may include a pressure sensor that is configured to sense the pressure at the blunt tip of the needle member 102 as it engages with the various bodily tissues, and an injection member that is configured to inject the dissection fluid through the lumen of the needle member 102 into the desired location when the sensed pressure decreases below the tissue pressure. For example, the pressure sensor may sense when the needle member 102 enters a space having an intrinsic pressure less than the pressure of the tissue superficial to the desired space. In one example, for vaginal tissue dissection, the blunt tip and the opening of the needle member 102 may be inserted into the VVS or the RVS. As the blunt tip of the needle member 102 is penetrating the tissue layers before reaching the VVS or the RVS, the pressure sensor may sense that the pressure in the tissue is higher than for the VVS or RVS, however, when the blunt tip of the needle member 102 perforates the paravaginal fascia he/she may sense a change in resistance to advancement of the needle member 102 associated with a tactile and/or audible "pop," followed by a loss of tissue resistance. However, the operator may or may not feel the change in tissue resistance or the change in tissue pressure. As such, in one example, when the pressure decreases below the tissue pressure level, the injection member may automatically inject the dissection fluid into the VVS or RVS via the needle member 102. For example, the operator may not have to rely on his/her judgment of when they entered the space and can safely inject the dissection fluid. Rather, the LOR injection assembly may sense the drop in tissue pressure, and automatically inject the dissection fluid into the VVS or the RVS.

The insertion member 104 may be configured to be inserted into a body opening of the patient such a vagina, or an anal canal, for example. In one example, the insertion member 104 is capable of expanding the body opening once the insertion member 104 is inserted into the body opening. The needle member 102 may be movably coupled to the insertion member 104. For example, the needle member 102 may be coupled to the insertion member 104 in a manner such that the needle member 102 may move with respect to the insertion member 104.

In one example, because the vaginal wall is relatively thin (e.g., 3-5 mm), a small millimeter-sized movement of the needle member 102 can translate into a relatively large proportional movement through the vagina. As such, in one example, the needle member 102 may be moveable coupled to the insertion member 104 in such a manner that the needle member 102 is inclined with respect to the plane of the vaginal wall. This inclination may increase the functional length of the tunnel and reduce the vertical travel relative to the needle tip movement as it is advanced through the tissue. In other words, the needle member 102 may be moveable coupled to the insertion member 104 such that the blunt tip of the needle member 102 advances into the vaginal wall at an angle. In one embodiment, the angle of insertion with respect to the plane of the vaginal wall is approximately 15 degrees. However, the embodiments encompass any value for the angle of insertion.

The needle member 102 may be moveable coupled to the insertion member 104 to ensure that the needle member 102 is properly oriented in regards to having the convex side of the needle member 102 facing away from the vaginal lumen and angled appropriately to ensure a long needle path that would dampen needle tip movements in the Z-axis (perpendicular to the plane of the vagina).

In one example, the needle member 102 may be initially coupled to the insertion member 104 such that the needle member 102 is in a retracted position. Then, the insertion member 104 may be inserted into the body opening. Once the insertion member 104 is inserted into its desired location within the body opening, the operator may move the needle member 102 from the retracted position to pierce one or more tissue layers until reaching its desired depth. Once the needle member 102 is at its desired depth, the needle member 102 (via its opening) may discharge dissection fluid to a location within the body area such as the VVS or RVS.

In other embodiments, the needle member 102 may be part of another assembly such as the injection assembly. In this manner, the needle member 102 may be moveably coupled to the insertion member 104 via the injection assembly. In this manner, the injection assembly (and at least a portion of the needle member 102) may be moveably coupled to the insertion member 104. For example, the injection assembly may be coupled to the insertion member 104 in a manner that positions the needle member 102 in the proper orientation to allow for an angled insertion into the tissue layers with respect to the plane of the vagina.

In some embodiments, the insertion member 104 may include a device having a wedged-shaped portion configured to grasp a portion of tissue when inserted into the body opening. The wedged-shaped portion may have a triangular shape. In one example, the wedged-shaped portion may define a slot that engages the portion of tissue when inserted into the body opening. In one example, the slot may begin at a distal edge of the wedged-shaped portion and extend into the wedged-shaped portion. In one example, the slot may be rectangular in shape. However, the slot may encompass any type of shape. The slot of the wedged-shaped portion may allow a portion of the vaginal wall to be grasped, and then pulled within the slot.

Also, the wedged-shaped portion may define a lumen extending from a first opening on the proximate end of the wedged-shaped portion to a second opening on the distal end of the wedged-shaped portion. In one example, the lumen of the wedged-shaped portion may extend in a line that is parallel with a slope of the wedged-shaped portion. The blunt tip of the needle member 102 may be inserted into the lumen at the first opening through the second opening. The orientation of the lumen of the wedged-shaped portion may ensure the proper orientation of insertion into the bodily tissue.

In further embodiments, the device having the wedged-shaped portion may also include an elongated member and a base. The wedged-shaped portion may be coupled to one end of the elongated member, and the base may be coupled to the other end of the elongated member. In one example, the elongated member may be designed such that the needle member 102 may be moveable coupled to the elongated member such that the blunt tip of the needle member 102 enters the first opening, extends through the lumen of the wedged-shaped portion, and may exit the second opening. As the needle member 102 is further moved in this manner, the blunt tip of the needle member 102 may pierce the bodily tissue that engages the slot on the wedged-shaped portion. In a further example, the elongated member may include a groove (e.g., u-shaped groove) extending from a distal end of the elongated member to a proximate end of the elongated member, and the u-shaped groove is configured to engage one or more portions of the needle member 102 and/or the injection assembly having the needle member 102.

In some embodiments, the insertion member 104 may include a speculum. In some embodiments, the speculum can be a vaginal speculum configured for vaginal inspection/examination. In some other embodiments, the insertion member 104 may be an expandable speculum such that the speculum expands when inserted into the body. In one example, the insertion member 104 may be a set of blades or flaps that are configured to expand or collapse with respect to each other. For example, the insertion member 104 may include a first blade member and a second blade member, where at least one of the blade members are configured to move with respect to the other one. In this example, the needle member 102 may be movably coupled to one of the first blade member and the second blade member.

In another embodiment, the first blade member or the second blade member may define a slot on its distal end that is configured to receive bodily tissue when inserted into the body of the patient. In this embodiment, the blade member having the defined slot may be moveable coupled to the needle member 102. The slot of the blade member may allow a portion of the vaginal wall to be grasped, and then pulled within the slot. When the expandable speculum is opened, the expansion of the speculum may create a counter force that would push the deeper organ layers away and help create a distraction force to facilitate the insertion of the needle member 102 and subsequent injection.

Figure 2A:
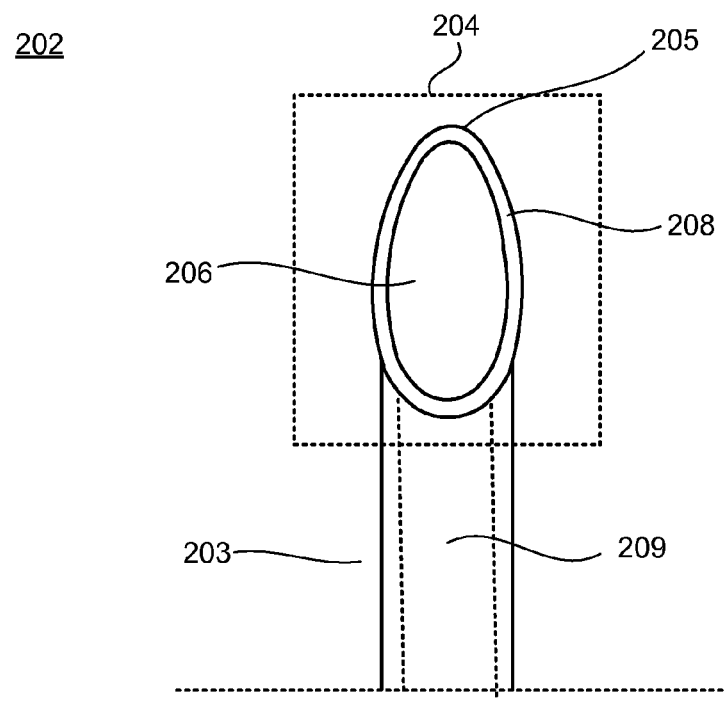
FIG. 2A illustrates a front view of a needle member according to an embodiment.

FIG. 2A illustrates a front view of a needle member 202 according to an embodiment. In this example, the needle member 202 may be considered a Tuohy needle or Tuohy-based needle. The needle member 202 may include an elongated member 203 having a distal end portion 204. The elongated member 203 has a circular structure (with a hollow interior—a lumen 209) that extends from a proximate end portion (not shown) to the distal end portion 204. The distal end portion 204 may include a blunt tip 205, needle circumference portion 208, and an opening 206. Further, the needle member 202 may include a lumen 209 extending along the length of the needle member 202 from a proximate end (not shown) of the needle member 202 to the opening 206 disposed proximate to the blunt tip 205 on the distal end portion 204 of the needle member 202.

In one example, the blunt tip 205 may be rounded or substantially rounded. The needle circumference portion 208 may be a boundary of the opening 206. In one example, the opening 206 may be a bevel surrounding the opening 206. The bevel may have a convex shape. In one example, the needle circumference portion 208 may be substantially oval. In other examples, the needle circumference portion 208 may be circular. As further described below, the opening 206 may discharge the dissection fluid from the lumen 209 into the desired location within the body of the patient. The opening 206 may be considered a side port or a port located substantially on the side of the needle member 202.

Figure 2B:
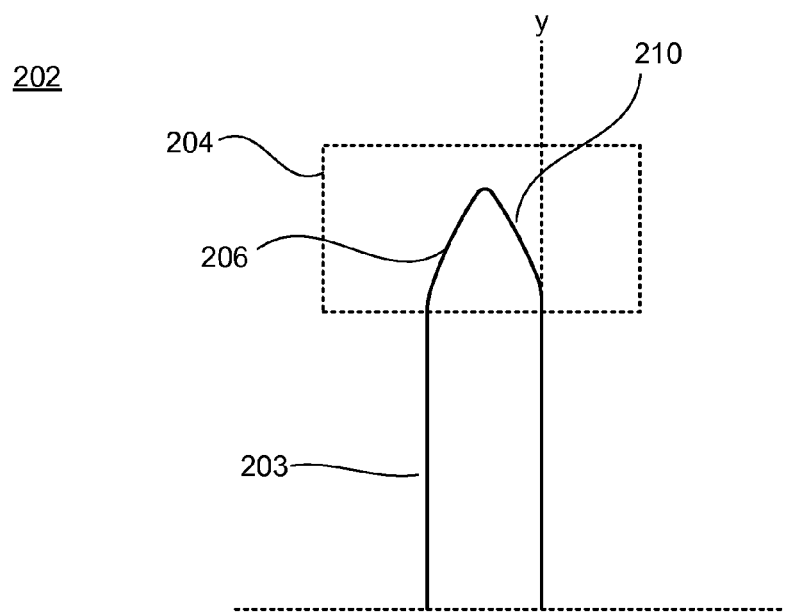
FIG. 2B illustrates a side view of the needle member of FIG. 2A according to an embodiment.

FIG. 2B illustrates a side view of the needle member 202 of FIG. 2A according to an embodiment. As shown in FIG. 2B, the distal end portion 204 of the needle member 202 may include a bent portion 210. For example, without the bent portion 210, one side (Y) of the elongated member 203 of the needle member 202 may extend in the Y-direction, as indicated by the letter Y shown in FIG. 2B. However, in this embodiment, the distal end portion 204 (or a portion thereof) may be curved or bent. The bent portion 210 may define the opening 206.

FIGS. 3A-3D illustrates various positions of a needle member 302 within the tissue layers according to an embodiment. The needle member 302 may be the needle member 102 of FIG. 1 or the needle member 202 of FIGS. 2A and 2B. For example, as discussed above, because the needle member 302 may include a blunt tip having a configuration that allows insertion through some tissue layers, but relatively harder insertion through other deeper tissue layers, the depth of the insertion of the needle member 302 may be controlled.

Figure 3A:
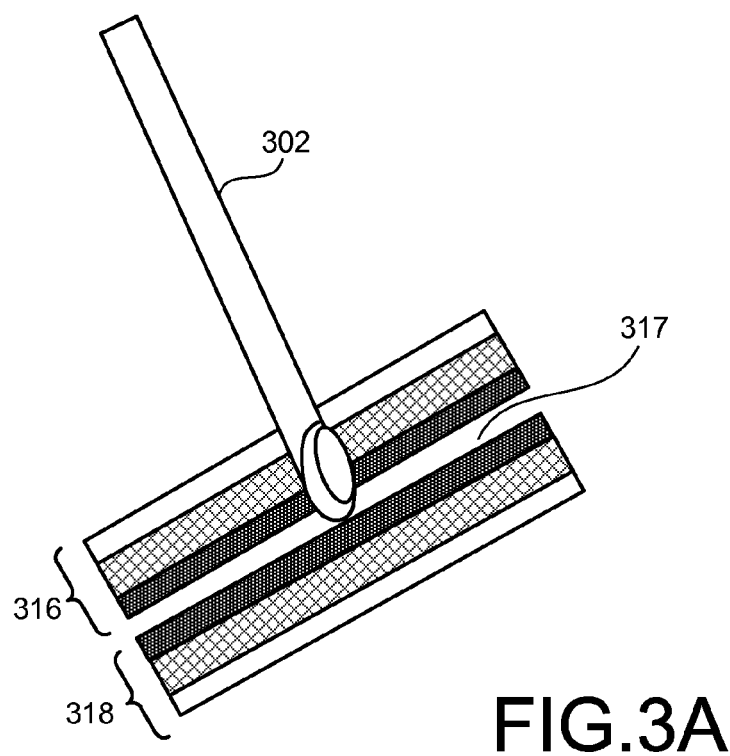
FIG. 3A illustrates a position of the blunt tip of the needle member within a space according to an embodiment.

FIG. 3A illustrates a position of the blunt tip of the needle member 302 within a space 317 according to an embodiment. In one example, the space 317 may be the VVS or RVS. However, generally, the space 317 may be any possible area between tissue layers. Before reaching the space 317, the blunt tip of the needle member 302 must penetrate a plurality of tissue layers 316. In one example, the plurality of tissue layers 316 may include the vaginal muscosa, the vaginal muscle, and the paravaginal fascia. However, the embodiments are not limited to three layers, where the needle member 302 may penetrate any number of tissue layers 316 including one, two, or more than three.

As shown in FIG. 3A, the blunt tip of the needle member 302 may be inserted through the plurality of tissue layers 316 until reaching the space 317. Behind the space 317, a plurality of tissue layers 318 may exist that should not be penetrated by the needle member 302. In one example, the plurality of tissue layers 318 may include the paravesical fascia, the bladder muscle, and the bladder muscosa. In another example, the plurality of tissue layers 318 may be the paravesical fascia, the rectal muscle, and the rectal mucosa.

Using a conventional sharp tip needle, it may be impossible or very difficult to pass the injection needle through the vaginal wall (e.g., the vaginal muscosa, the vaginal muscle, and the paravaginal fascia) without going into at least one of the plurality of deeper tissue layers 318 such as the paravesical fascia and the (bladder or rectal) muscle. For example, the vaginal wall may be 4 mm (plus or minus 1 mm), and the fascia layers may be about 1 mm thick. Because of operator fear of injury to either the bowel or bladder, the injections usually fall short of the ideal depth (e.g., with the needle lumen situated in the space). As a result, when fluid is injected with the intent of opening the space, because of a plane being created within the vaginal wall (e.g., due to the injection of dissection fluid within the vaginal wall—not the VVS or RVS), which may cause problems such as vaginal mesh exposure. In other words, vaginal mesh exposure may be the consequence of not performing the hydrodissection within the VVS or the RVS.

In addition, unless the operator is very careful, by the time the opening of the conventional sharp needle is located in the VVS or the RVS, the piercing tip (part of the lumen) may span from the vaginal muscularis all the way through the paravesical or the pararectal fascia. This may result in dissection fluid entering into the muscular walls rather than between the vaginal and visceral fascia layers, which may complicate dissection.

Figure 3B:
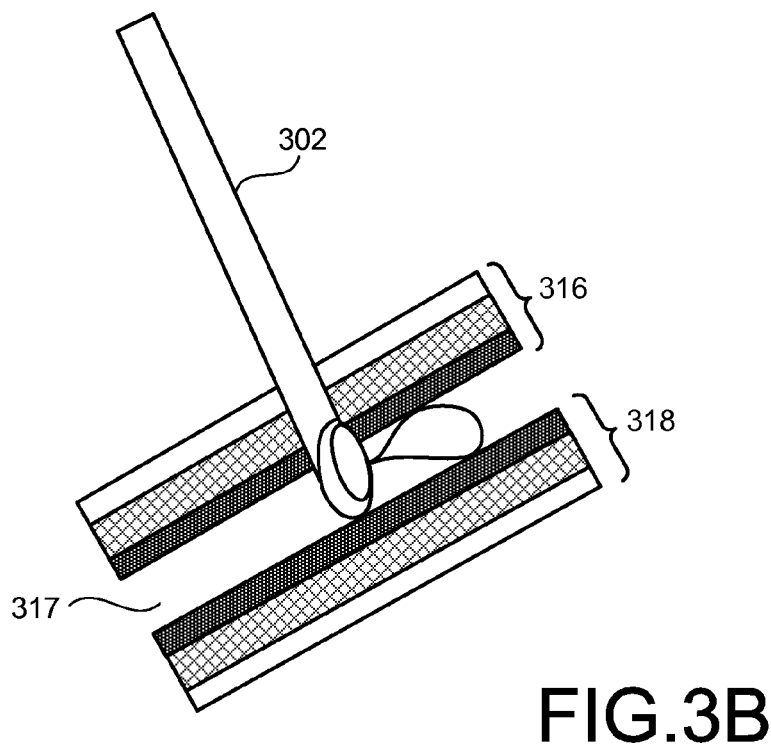
FIG. 3B illustrates a position of the blunt tip and the opening of the needle member within the space according to an embodiment.

FIG. 3B illustrates a position of the blunt tip and the opening of the needle member 302 within the space 317 according to an embodiment. For example, as the distal end portion of the needle member 302 is inserted into the space 317, the opening of the needle member 302 discharges the dissection fluid into the space 317, thereby creating an actual space within the VVS or the RVS. Also, due to the orientation of the opening (substantially located on the side of the needle member 302), the projection of dissection fluid may be relatively more accurate in terms of creating a space between a plane of the paravesical fascia and a plane of the paravaginal fascia as opposed to projecting the dissection fluid within other planes of the vaginal wall.

Figure 3C:
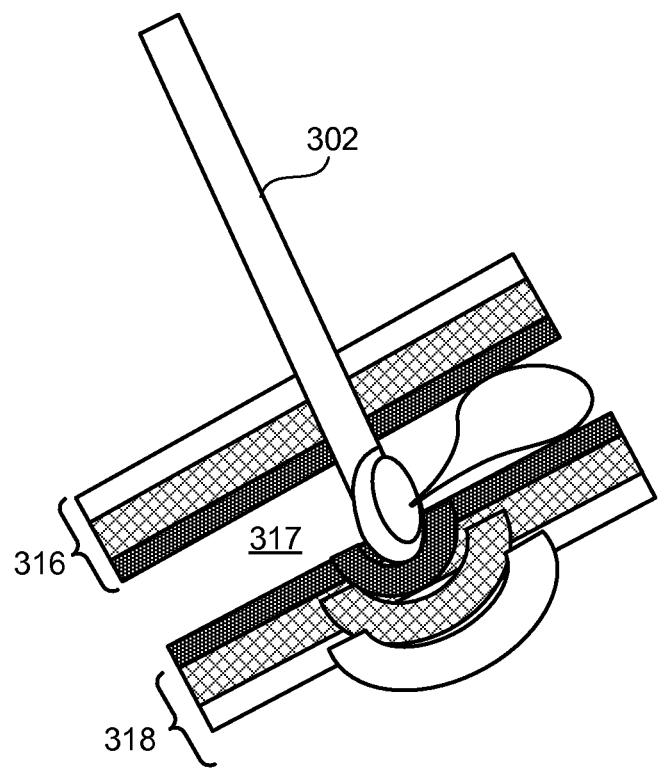
FIG. 3C illustrates a position of the blunt tip of the needle member that extends beyond the space according to an embodiment.

FIG. 3C illustrates a position of the blunt tip of the needle member 302 that extends beyond the space 317 according to an embodiment. For example, in contrast to the conventional sharp needle, as the blunt tip of the needle member 302 is inserted further into the body of the patient (e.g. beyond its desired location), the blunt tip of the needle member 302 pushes the deeper tissue layers away (as opposed to piercing them). For example, the blunt tip of the needle member 302 may push the paravesical fascia, and the (rectal or bladder) muscle away.

However, in this example, the opening of the needle member 302 is correctly positioned within the correct plane for hydrodissection, e.g., substantially most of the opening of the needle member 302 is located within the space 317. As such, if the opening of the needle member 302 is within the correct plane (as shown in FIG. 3C), the increase in fluid pressure causes the dissection fluid to spread out laterally, e.g., it atraumatically dissects the open space. Again, if it is not in the correct plane (which happens more often with conventional sharp point needles), the tissue may get more edematous and the space opens poorly.

Figure 4:
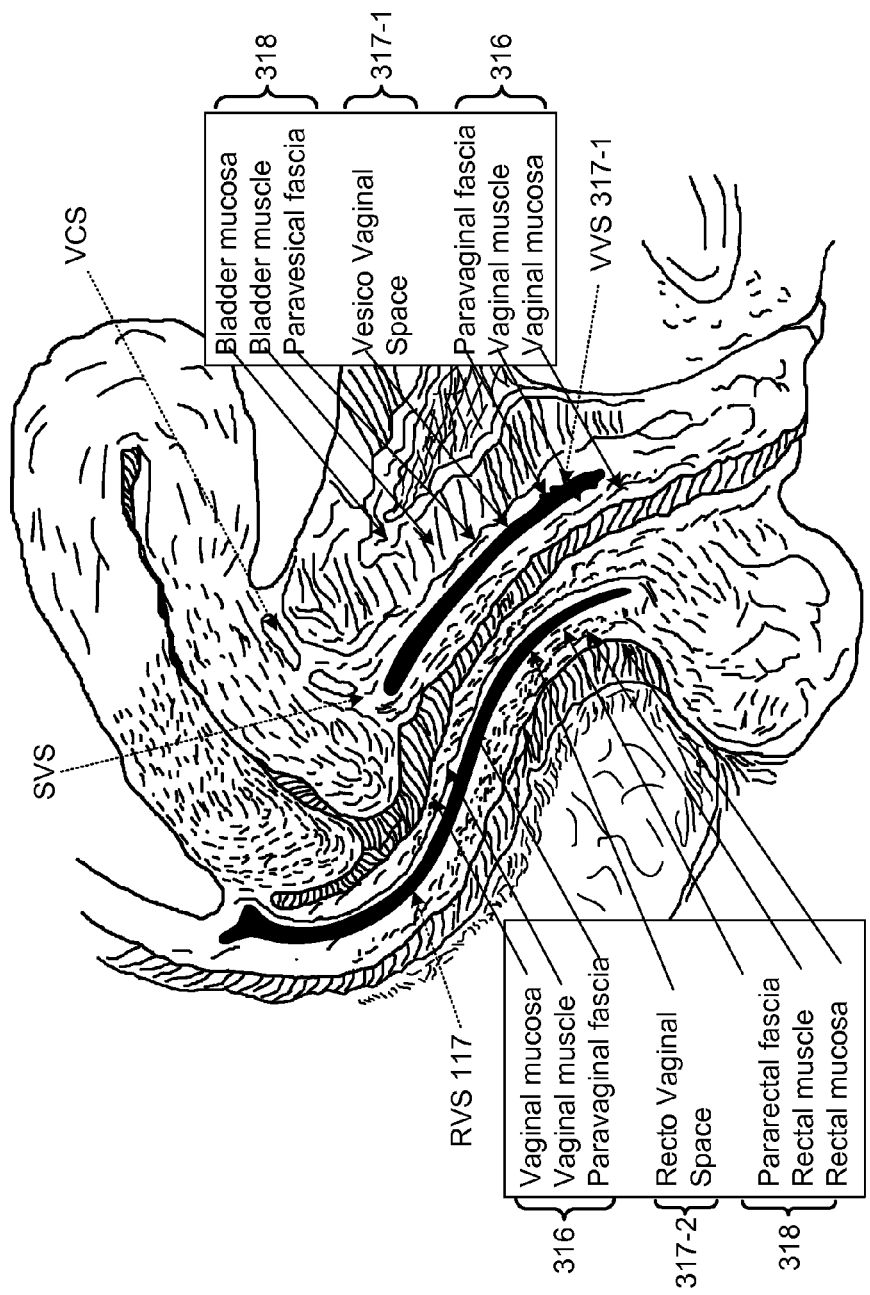
FIG. 4 illustrates a side view of the female pelvis showing the different tissue layers and spaces around the vagina.

FIG. 4 illustrates a side view of the female pelvis showing the different tissue layers and spaces around the vagina. On the front side of the vagina (e.g., the bladder rests on the front side), the tissue layers 316 may include the vaginal muscosa, the vaginal muscle, and the paravaginal fascia. Then, the Vesico Vaginal Space (VVS) 317-1 may exist on a side of the paravaginal fascia. Beyond the VVS 317-1, the tissue layers 318 may include the paravesical fascia, the bladder muscle, and the bladder muscosa. On the back side of the vagina, the tissue layers 316 may include the vaginal mucosa, the vaginal muscle, and the paravaginal fascia. Then, the Recto Vaginal Space 317-2 may exist on the side of the paravaginal fascia. Beyond the RVS 317-2, the tissue layers 318 may include the pararectal fascia, the rectal muscle, and the rectal muscosa.

In further detail, the bladder is enveloped by a layer of connective tissue called the paravesical fascia. Similarly, the vagina is surrounded by two sheets of connective tissue that run from pelvic sidewall to pelvic sidewall. Anteriorly, the tissue is called the anterior paravaginal fascia. This sheet of fascia runs from the pubic bone up to the cervix where it merges into the supravaginal septum (SVS). It is also referred to as the pubocervical fascia. On the back side of the vagina, the tissue is called the posterior paravaginal fascia. This connective tissue layer is also called the rectovaginal fascia. The bladder rests on the front side of the vagina. This means that the paravesical fascia lies on the anterior paravaginal fascia. Similarly, the vagina lies over the rectum. As such, the posterior paravaginal fascia rests on the pararectal tissue. These relationships produce two spaces. The space anterior to the vagina is called the Vesico-Vaginal Septum (VVS) 317-1. The Recto-Vaginal Septum (RVS) 317-2 is the space between the back of the vagina and the front of the rectum.

If an operator can open up these spaces 317, it may create two unobstructed areas where pelvic floor mesh can be placed, either by a vaginal or abdominal means.

Figure 5:
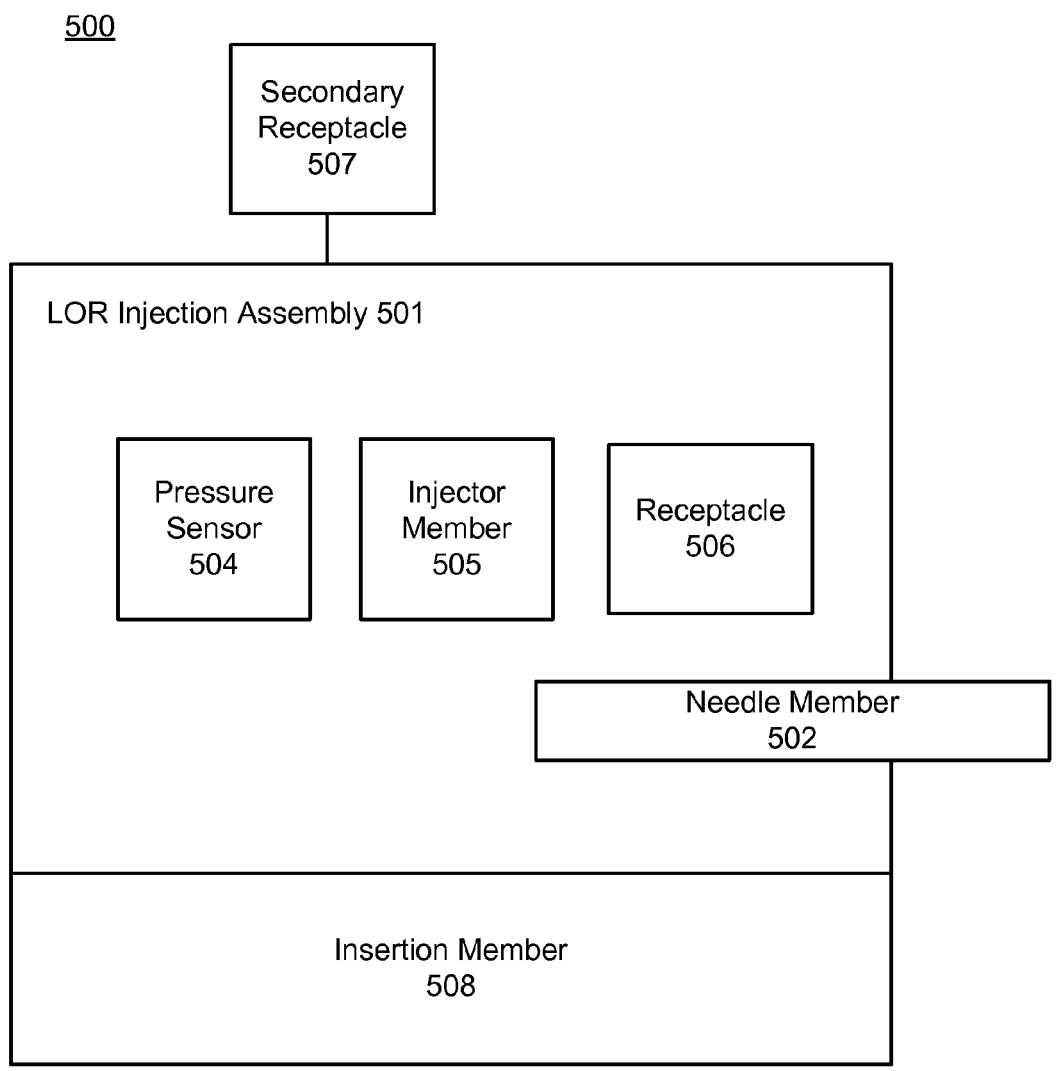
FIG. 5 is a schematic diagram of a medical device according to another embodiment.

FIG. 5 schematically illustrates a medical device 500 according to an embodiment. In one example, the medical device 500 may be used for opening up spaces before receiving the bodily implant (e.g., hydrodissection), before starting the dissection for a sacrocolpopexy, or any other procedure described herein. The medical device 500 may include a loss-of-resistance (LOR) injection assembly 501, and an insertion member 508. The insertion member 508 may be any type of insertion member discussed herein. The LOR injection assembly 501 may include a needle member 502, a pressure sensor 504, an injector member 505, and a receptacle 506. Additionally, the LOR injection assembly 501 may be associated with a secondary receptacle 507. In one example, the secondary receptacle 507 may store a larger amount of fluid than the receptacle 506. The needle member 502, the pressure sensor 504, the injector member 505, and the receptacle 506 may be embodied into a single enclosure, or multiple enclosures. For example, the LOR injection assembly 501 may include a structural member (e.g., a handle) enclosing one or more of the needle member 502, the pressure sensor 504, the injector member 505, and the receptacle 506.

The receptacle 506 maybe any type of reservoir capable of housing the dissection fluid. The receptacle 506 may be a syringe, distensible bladder, chamber, or generally any type of housing capable of housing dissection fluid. Also, the size of the receptacle 506 may vary. In one embodiment, the size of the receptacle 506 may be designed such that the dissection fluid may be injected into the space to fully develop the VVS and/or the RVS without replacing the receptacle 506 with another receptacle 506. For example, smaller-type syringes may typically hold 5 cc of fluid. Larger-type syringes may typically hold 20 or 30 cc of fluid. However, the volume of fluid used for vaginal hydrodissection may be over 100 cc of fluid. As such, for smaller-type syringes and larger-type syringes, syringe exchanges may be required to develop the appropriate amount of fluid to fully develop the space. However, the needle member 502 in a 3-5 mm thick vaginal wall can easily slip out of place during syringe exchanges. Therefore, in one embodiment, the receptacle 506 may be configured to hold 100 cc to 200 cc of dissection fluid in order to avoid syringe exchanges.

In one example, the receptacle 506 maybe a pressurized reservoir of dissection fluid. In this example, the receptacle 506 may be a fluid chamber having pressurized dissection fluid. The dissection fluid may be pressurized to a certain level such that when a drop of pressure is sensed (e.g., when the needle member 502 enters the space), the dissection fluid may be released from the fluid chamber to the space via the opening of the needle member 502.

In another embodiment, the LOR injection assembly 501 may be associated with multiple reservoirs of dissection fluid. For example, the LOR injection assembly 501 may be additionally associated with the secondary receptacle 507. The secondary receptacle 507 maybe any type of reservoir capable of housing the dissection fluid. The secondary receptacle 507 may be a syringe, distensible bladder, chamber, or generally any type of housing capable of housing dissection fluid. In one example, the dissection fluid stored in the secondary receptacle 507 may be pressurized. The secondary receptacle 507 may be coupled to the needle member 502 in the same manner as the receptacle 506, or the secondary receptacle 507 may be connected to the receptacle 506.

In one example, the receptacle 506 may store a lesser amount of dissection fluid than the secondary receptacle 507. In this context, the secondary receptacle 507 may store the volume of fluid used for vaginal hydrodissection, which may be over 100 cc of fluid. The receptacle 506 may store a relatively smaller amount of dissection fluid such as 5 cc or so. In this example, as the needle member 502 is inserted into the space, a drop in pressure is sensed, and the dissection fluid from the receptacle 506 may be released to the space via the needle member 502. For example, the pressure sensor 504 may sense a drop in pressure and then release the dissection fluid from the receptacle 506. In one example, the receptacle 506 may be the pressure sensor 504/injection member 505 if the receptacle 506 is a LOR device such as a spring-loaded syringe. Then, the release of the dissection fluid from the receptacle 506 may provide an indication to the operator that the needle member 502 has reached the space, and therefore the operator may stop the needle advancement. Because the operator has entered the desired space (and some dissection fluid has been released), the operator may further dissect the space by releasing the dissection fluid from the secondary receptacle 507, which contains a larger amount of dissection fluid. In this manner, the needle member 502 may remain in its correct place while fully dissecting the space without exchanging receptacles or syringes.

In another example, the dissection fluid from the secondary receptacle 507 may supply the receptacle 506. For example, after the receptacle 506 is loaded with dissection fluid from the secondary receptacle 507, the dissection fluid may be injected into the space, and then the dissection fluid from the secondary receptacle 507 may re-fill the empty receptacle 507. Also, the receptacle 506 may be included within a structural member of the LOR injection assembly 501, where the secondary receptacle 507 may be coupled to the LOR injection assembly 501 but located outside the structural member of the LOR injection assembly 501. In other examples, both the receptacle 506 and the secondary receptacle 507 may be located within the structural member of the LOR injection assembly 501 or outside the structural member of the LOR injection assembly 501.

In one example, the LOR injection assembly 501 may be coupled to at least a portion of the needle member 502. In one example, a portion of the needle member 502 may be fixed to the LOR injection assembly 501. In other examples, the portion of the needle member 502 may be moveably coupled to the LOR injection assembly 501. The needle member 502 may be the same needle member described with respect to any of the previous figures.

In one example, the LOR injection assembly 501 may be moveably coupled to the insertion member 508. For example, the LOR injection assembly 501 may be coupled to the insertion member 508 in a manner that the LOR injection assembly 501 is moveable in the direction of the insertion of the needle member 502 in the tissue layers. In this example, the LOR injection assembly 501 may be coupled to the insertion member 508 in a manner that positions the needle member 502 in the proper orientation to allow for an angled insertion into the tissue layers with respect to the plane of the vagina. In other words, the needle member 502 on the LOR injection assembly 501 may be moveable coupled to the insertion member 508 such that the blunt tip of the needle member 502 advances into the vaginal wall at an angle. In one embodiment, the angle of insertion with respect to the plane of the vaginal wall is approximately 15 degrees. However, the embodiments encompass any value for the angle of insertion. The structure of the LOR injection assembly 501 fitting with the structure of the insertion member 508 may ensure that the needle member 502 is properly oriented in regards to having the convex side of the needle member 102 facing away from the vaginal lumen and angled appropriately to ensure a long needle path that would dampen needle tip movements in the Z-axis (perpendicular to the plane of the vagina).

The LOR injection assembly 501 may be a device that senses when the needle member 502 has entered into a space. For example, the LOR injection assembly 501 may be configured to sense a drop in tissue pressure or loss of resistance during advancement of the needle member 502. In one example, the LOR injection assembly 501 may automatically inject the dissection fluid upon sensing the space. In another example, the LOR injection assembly 501 may provide visual feedback upon entering the space, and then based on an operator's action, inject the dissection fluid. In another example, the LOR injection assembly 501 may stop further advancement of the needle member 502 until some dissection fluid has been injected to begin opening up the space. In one embodiment, the injection of 5-10 cc of dissection fluid may release the hold to permit movement of the needle member 502. For example, upon sensing that the needle member 502 has entered the space, the LOR injection assembly 501 may stop movement of the needle member 502. Then, after at least some dissection fluid has been injected, the LOR injection assembly 501 may release the hold, and allow further movement of the needle member 502. In another example, the LOR injection assembly 501 may identify when to stop the needle advancement. For example, some dissection fluid may leave the receptacle The LOR injection assembly 501 may include a pressure sensor 504 and an injector member 505. The pressure sensor 504 may be configured to sense the tissue pressure of the tissue layers on a distal end of the needle member 502 during advancement of the needle member 502. For example, the pressure sensor 504 may sense the tissue pressure of the tissue layers as the needle member 502 is being inserted into the body of the patient. The pressure sensor 504 may be configured to compare the tissue pressure with a certain pressure level, and when the pressure drops below the pressure level, the pressure sensor 504 may indicate that the needle member 502 has entered into the space. For example, the pressure sensor 504 may sense when the needle member 502 enters a space having an intrinsic pressure less than the pressure of the tissue superficial to the desired space. In one example, the pressure sensor 504 may provide visual feedback to the operator showing that the needle member 502 has entered the space. Generally, the visual feedback may be any type of indicator. For example, an operator may be able to view the discharging of the dissection fluid from the receptacle 506 and/or the secondary receptacle 507. In one example, the dissection fluid may be colored in a manner that makes the dissection fluid easy to see from within the receptacle 506, the secondary receptacle 507 and/or any other components in which the dissection fluid may be transferred. Also, the pressure sensor 504 may be associated with a component that provides visual feedback to the operator of entering the space such as movement of a component associated with the pressure sensor 504 and/or the receptacle 506, a decreased size of the receptacle 506 and/or the secondary receptacle 507, and/or generation of an alarm (e.g., sound, visual display).

In one example, the pressure sensor 504 may be any type of pressure sensor such as a pressure-based mechanism, electrical-based mechanism, and/or generally any type of pressure sensor. In one embodiment, the pressure sensor 504 may be a spring-based mechanism having a spring. The spring may be associated with a spring constant. In this example, the spring constant may be set to be equal to or slightly lower than the tissue pressure of the vaginal wall (e.g., the vaginal mucosa, the vaginal muscle, and the paravaginal fascia), but sufficiently high enough to allow the dissection fluid to be released into the spaces, e.g., the VVS and the RVS. That is, when the opening or lumen of the needle member 502 is located within the vaginal wall, no dissection fluid may flow. However, when the opening or lumen of the needle member 502 is located within the space beyond the vaginal wall, the pressure drops below the spring constant, the spring-based mechanism is configured to release the dissection fluid from the receptacle 506.

In other examples, the pressure sensor 504 may be a container of compressed gas (e.g., air, $CO_2$), which, when filled produces the pressure akin to the spring constant explained above. As such, when the pressure drops (e.g., when the needle member 502 enters the space), the compressed gas may drive the dissection fluid from the receptacle 506 into the space. Further, the container of compressed gas may be associated with an indicator providing a visual indication of when the needle member 502 enters the space.

In other examples, the pressure sensor 504 maybe embodied into the receptacle 506. For example, the pressure sensor 504 may be a LOR syringe having a spring associated with a spring constant. When the tissue pressure drops below the spring constant, the dissection fluid is injected from the LOR syringe. Also, the pressure sensor 504 may include a pressure chamber filed with pressured dissection fluid having a pressure akin to the spring constant explained above. The pressure chamber may provide a visual indication of when the needle member 502 enters the space, and may further drive the dissection fluid into from the receptacle 506 to the space. In other examples, the pressure sensor 504 may include a distensible bladder which, when filled produces pressure akin to the spring constant explained above. This distensible bladder may be a cylindrical chamber where one end of the cylinder is located on the surface of the LOR injection assembly 501. The portion that is located on the surface of the LOR injection assembly 501 may be a distensible membrane. When the receptacle 506 is filled of fluid, the membrane would bulge up above the surface of the LOR injection assembly 501. Upon reaching the space, the convex curve of the "bubble" may flatten (as the fluid is drained into the space), thereby giving visual feedback to the operator.

In other examples, the pressure sensor 504 may be any type of electronic tissue pressure sensor that senses the tissue pressure during advancement of the needle member 502. For example, the electronic tissue pressure may include electronic components configured to sense the tissue pressure, and determine when the tissue pressure drops below a certain predetermined pressure level.

The injector member 505 may be any type of mechanism that injects the dissection fluid from the receptacle 506 and/or the needle member 502 into the space. The injector member 505 may be any type of mechanism such as pressurized pumps, automatic pumps, valves, or generally having type of mechanism capable of driving fluid from one area to another area.

Figure 6A:
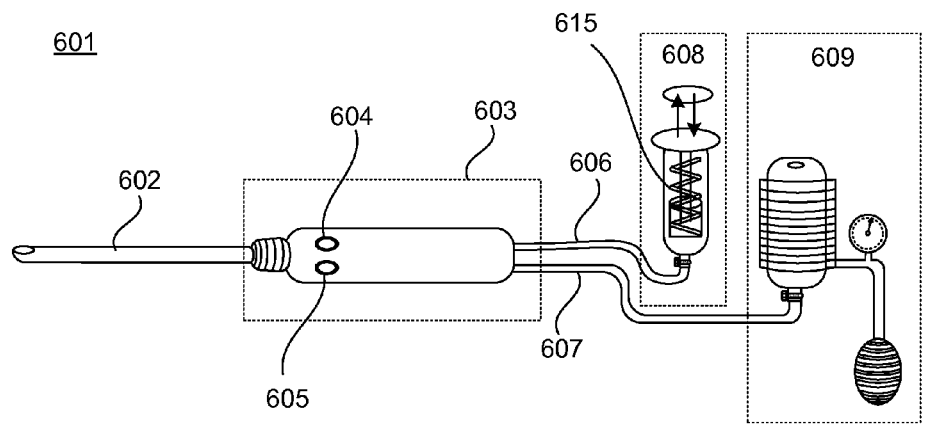
FIG. 6A illustrates a perspective of a loss-of-resistance (LOR) injection assembly according to an embodiment.

FIG. 6A illustrates a perspective of a LOR injection assembly 601 according to an embodiment. In one example, the LOR injection assembly 601 may be used for opening up spaces before receiving the bodily implant, before starting the dissection for a sacrocolpopexy, or any other type of procedure described herein. The LOR injection assembly 601 may be coupled to any one of the insertion members as previously described, or any one of the insertion members described with reference to FIGS. 8-10.

Referring to FIG. 6A, the LOR injection assembly 601 may include a needle member 602, a LOR handle 603, a first receptacle 608 storing the dissection fluid, and a second receptacle 609 storing pressurized solution. The second receptacle 609 may store a larger amount of fluid than the first receptacle 608. For example, the second receptacle 609 may store enough solution to fully develop the VVS or RVS. In one example, the pressurized solution may be pressurized saline solution. The needle member 602 may be any of the needle members previously described. Also, the LOR injection assembly 601 may include a portion of a dissection fluid line 606 that connects to the first receptacle 608 for transferring the dissection fluid from the first receptacle 608 to the LOR handle 603, and a portion of a pressurized solution line 607 that connects to the second receptacle 609 for transferring the pressurized fluid from the second receptacle 609 to the LOR handle 603.

Further, the LOR handle or hub or hub member 603 may include a first button 604 configured to release the dissection fluids (when depressed) from the first receptacle 608 to the space via the dissection fluid line 606 and the needle member 602, and a second button 605 configured to release (when depressed) the pressured solution to the needle member 602 via the pressurized solution line 607. As shown with respect to FIG. 6B, the dissection fluid line 606 may be coupled to the first button 604, which controls the transfer of the dissection fluid. Also, the pressurized solution line 607 may be coupled to the second button 605, which controls the transfer of the pressurized solution.

In one example, the first receptacle 608 may be a loss of resistance container (e.g., syringe) that is a spring-loaded device. For example, the first receptacle 608 may include a compression spring 615. In this example, the dissection fluid drawn up into the first receptacle 608 may empty only when the needle member 602 enters a space with a relatively low tissue pressure, e.g., less than the spring constant associated with the compression spring 615. In other examples, the first receptacle 608 may be another pressurized receptacle.

Figure 6B:
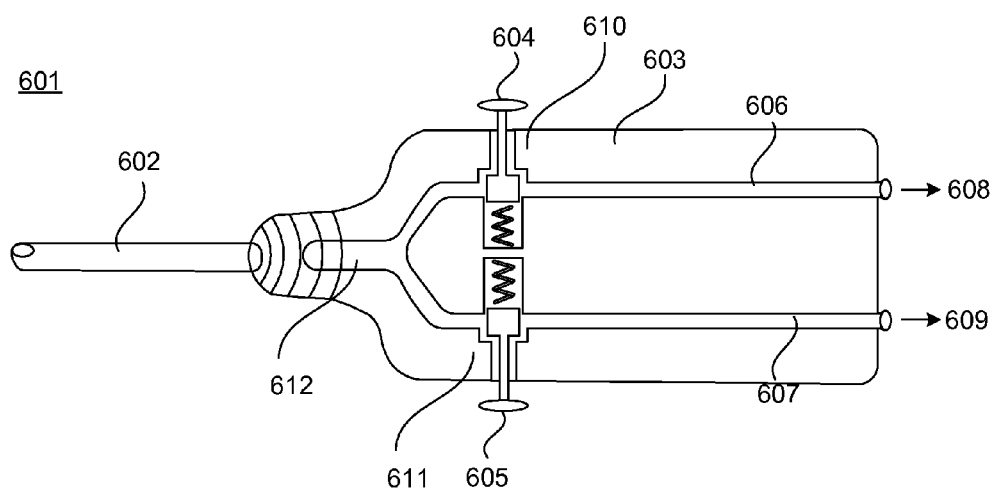
FIG. 6B illustrates a perspective of a LOR handle of the LOR injection assembly of FIG. 6A according to an embodiment.

FIG. 6B illustrates a perspective of the LOR handle 603 of the LOR injection assembly 601 of FIG. 6A according to an embodiment. In this example, the LOR handle 603 may include a first spring-valve mechanism 610 associated with the first button 604 for controlling the dissection fluid from the first receptacle 608, and a second spring-valve mechanism 611 associated with the second button 605 for controlling the pressurized solution from the second receptacle 609. For example, when the first button 604 is depressed, the pressure applied to the first button 604 drives the valve against the pressure of the spring to open the dissection fluid line 606 to a common portion 612 that eventually leads to the needle member 602. When the second button 605 is depressed, the pressure applied to the second button 605 drives the valve against the pressure of the spring to open the pressurized solution line 607 to the common portion 612 that eventually leads to the needle member 602.

In operation, an operator may couple the LOR handle 603 to an insertion member, and insert the insertion member into the body of a patient. As indicated above, the coupling of the LOR handle 603 to the insertion member may allow the blunt tip of the needle member 602 to insert into the vaginal wall at the appropriate angle. Then, as the blunt tip reaches the vaginal wall (e.g., the vaginal muscle, vaginal mucosa), the operator may depress the first button 604. However, at this time, dissection fluid is not released from the first receptacle 608 because the pressure has not dropped below the spring constant of the first receptacle 608.

Next, as the needle member 602 reaches the space (e.g., VVS or RCS), the pressure drops below the spring constant of the first receptacle 608, and the dissection fluid is released from the first receptacle 608 in the manner described above. The release of the first receptacle 608 may provide the operator with a visual indicator that the needle as entered the space. As this time, the dissection fluid may flow from the first receptacle 608 to the needle member 602 via the dissection fluid line 606. Next, the operator may release the first button 604, and depress the second button 605, which releases the pressurized solution from the second receptacle 609 to the needle member 602, thereby further driving the dissection fluid into the space. It is noted that the first receptacle 608 may have to be refilled (or exchanged), but the configuration of the LOR injection assembly 601 allows the needle member 602 to be unaffected by the refilling or replacement of the first receptacle 608.

Figure 7:
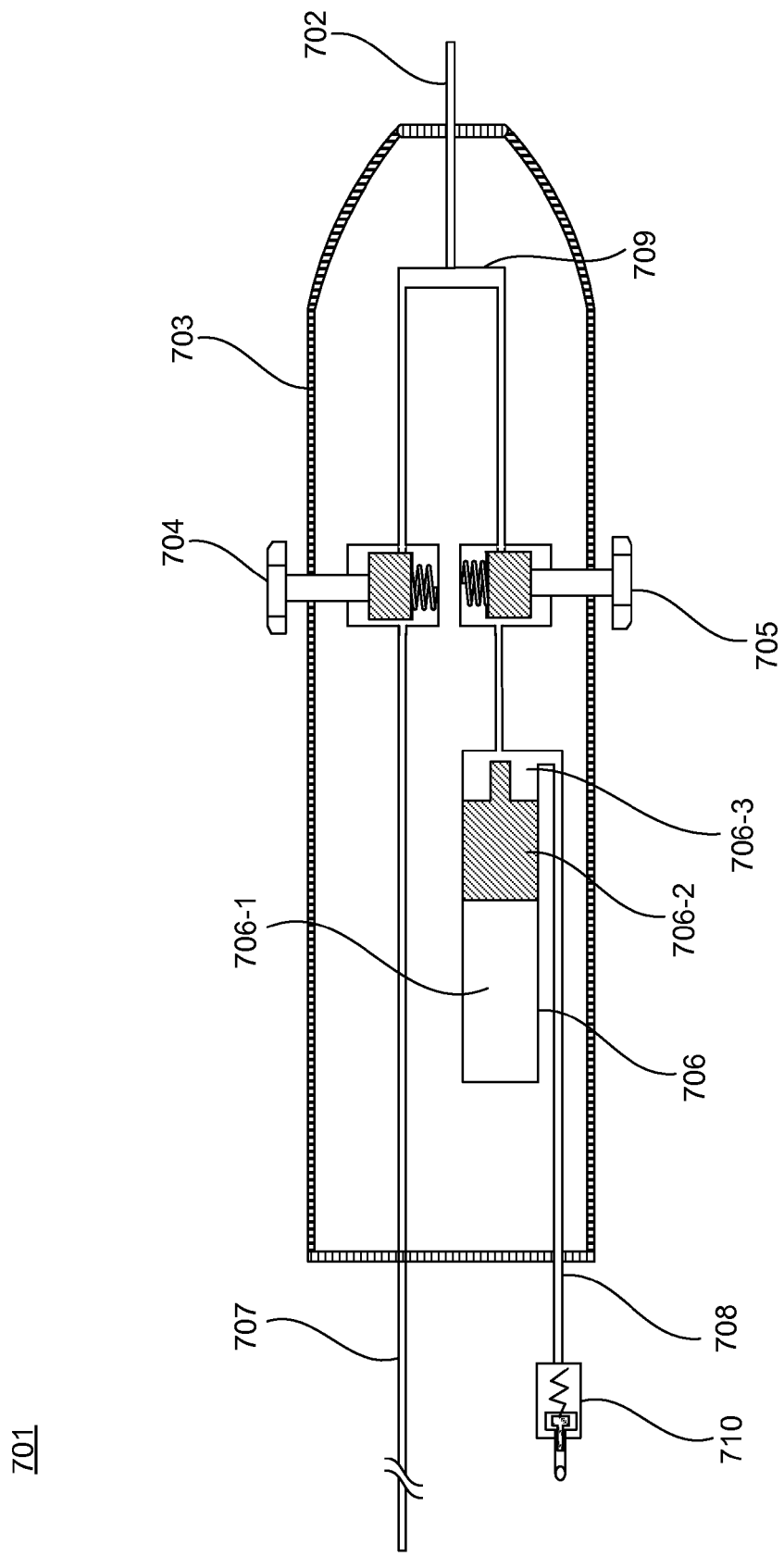
FIG. 7 illustrates a LOR injection assembly according to another embodiment.

FIG. 7 illustrates a LOR injection assembly 701 according to another embodiment. In one example, the LOR injection assembly 701 may be used for opening up spaces before receiving the bodily implant, before starting the dissection for a sacrocolpopexy, or any other procedure described herein. The LOR injection assembly 701 may be coupled to any one of the insertion members as previously described, or any one of the insertion members described with reference to FIGS. 8-10.

The LOR injection assembly 701 may include a structure 703 including at least a portion of a needle member 702, a first spring-loaded valve 704, a second spring-loaded valve 705, a pressurized solution line 707, a dissection fluid line 708, and an LOR pressure chamber 706 having a pressurized portion 706-1, a spacer 706-2, and a fluid receptacle portion 706-3. The structure 703 may be any type of structure that is configured to be coupled to an insertion member in a manner that positions the blunt tip of the needle member 702 according to the desired insertion angle. At least a portion of the needle member 702 may be coupled to the structure 703 such that the distal end of the needle member 702 is exposed outside the structure 703.

The first spring-loaded valve 704 may be coupled to a portion of the pressurized solution line 707. For example, the first spring-loaded valve 704 may control the transfer of pressurized solution from a receptacle (not shown) to the needle member 702 via the pressurized solution line 707 at the area where the first spring-loaded valve 704 is coupled to the pressurized solution line 707. One end of the pressurized solution line 707 is coupled to a receptacle (not shown) storing pressurized solution, and the other end of the pressurized solution line 707 is coupled to a common portion 709, which eventually leads to the lumen of the needle member 702. The first spring-loaded valve 704 is disposed at a location between the ends of the pressurized solution line 707. In one embodiment, the pressurized solution may be pressurized saline solution.

The second spring-loaded valve 705 may be coupled to a portion of the dissection fluid line 708. For example, the second spring-loaded valve 705 may control the transfer of pressurized dissection fluid from the LOR pressure chamber 706 to the space via the dissection fluid line 708 and the needle member 702 at the area where the second spring-loaded valve 705 is coupled to the dissection fluid line 708. One end of the dissection fluid line 708 is coupled to a receptacle (not shown) storing dissection fluid. In this example, the receptacle storing dissection fluid may be capable of storing a larger amount of dissection fluid such as 10 cc to 200 cc. The other end of the dissection fluid line 708 may be coupled the needle member 702 via the common portion 709. A spring valve 710 (which is explained later), the LOR pressure chamber 706, and the second spring-loaded valve 705 may be disposed along the dissection fluid line 708. In one example, the spring valve 710 may be disposed outside (or alternatively inside) the structure 703 between the receptacle storing the dissection fluid and the LOR pressure chamber 706. The LOR pressure chamber 706 may be disposed between the spring valve 710, and the second spring-loaded valve 705. The second spring-loaded valve 705 may be disposed between the LOR pressure chamber 706, and the common portion 709 leading to the needle member 702.

The spring valve 710 may be configured to transfer the dissection fluid from the receptacle storing the dissection fluid, and pressurize the LOR pressure chamber 706. For example, the spring valve 710 may transfer a portion of the dissection fluid (e.g., 5 cc) from the receptacle to the LOR pressure chamber 706 and pressurize the LOR pressure chamber 706. For instance, initially, the spacer 706-2 may be positioned towards the distal end of the LOR pressure chamber 706. In one example, the spacer 706-2 may have a protrusion that prevents the spacer 706-2 to contacting the distal edge of the LOR pressure chamber 706. Initially, the fluid receptacle portion 706-1 may be relatively small because the fluid receptacle portion 706-1 may not initially contain any dissection fluid, and the pressurized portion 706-3 may be relatively larger because the pressurized portion 703-3 contains air or any other type of pressurized substance. As the spring valve 710 is activated, a portion of the dissection fluid is transferred from the receptacle to the LOR pressure chamber 706. As the dissection fluid is being transferred, the dissection fluid pushes the spacer 706-2 towards the proximate end of the LOR pressure chamber 706, thereby enlarging the fluid receptacle portion 706-3 (as it fills with solution) and compacting the pressurized portion 706-1.

In one embodiment, the LOR pressure chamber 706 is pressurized to a certain level that is akin to the spring constant explained above. For example, the LOR pressure chamber 706 includes pressurized dissection fluid having a pressure level that is less than the tissue pressure of the vaginal wall, but greater than the space. As such, when the operator advances the needle member 702 to the tissue layers of the vaginal wall, the operator may engage the second spring-loaded value 705. Then, as the operator continues to insert the needle member 702 until reaching the space, the LOR pressure chamber 706 is configured to release the pressurized dissection fluid because the pressure dropped below the pressure of the LOR pressure chamber 706. As a result, the spacer 706-2 may begin to move back to its original position since the dissection fluid is being released into the needle member 702.

In one example, the structure 703 may include a portion that permits the operator to view the movement of the spacer 706-2 within the LOR pressure chamber 706. As such, the operator may view when the needle member 702 enters the space. Once the spacer 70-2 had advanced to the edge of the LOR pressure chamber 706, the second spring-loaded valve 705 may be released, and the first spring-loaded valve 704 may be depressed. Upon activation of the first spring-loaded valve 704, the pressurized solution may be transferred from the receptacle storing the pressurized solution to the needle member 702 along the pressurized solution line 707 in order to deliver the portion of the dissection fluid contained in the LOR pressure chamber 706 to the space.

As discussed above, these operations may be accomplished without having to any syringe exchanges which may result in movement of the needle member 702, and the injection space may be lost or then created in the incorrect place.

FIGS. 8A-8E illustrates various perspectives of an insertion member 800 according to an embodiment. The insertion member 800 may be a medical device capable of being inserted into an opening of the body. In one example, the insertion member 800 may be inserted in the vagina and/or the rectal canal. Further, the insertion member 800 may be coupled to a needle member as previously described and/or the LOR injection assembly of FIGS. 5-7.

Figure 8A:
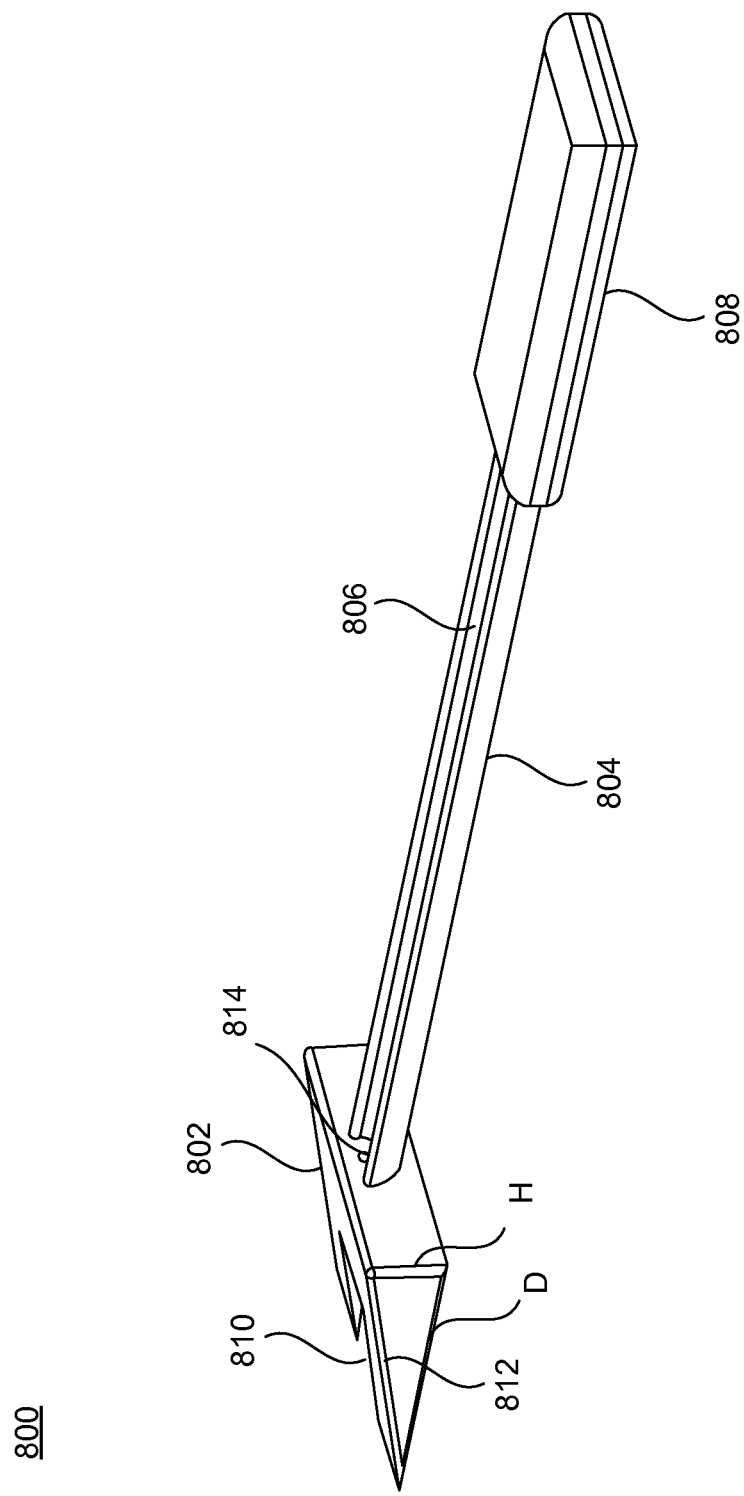
FIG. 8A illustrates a perspective of the insertion member according to an embodiment.
Figure 8B:
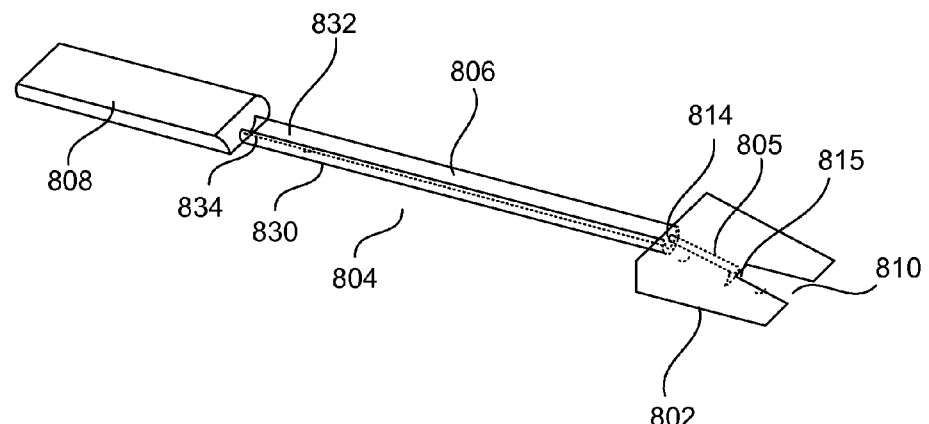
FIG. 8B illustrates another perspective of the insertion member according to an embodiment.
Figure 8C:
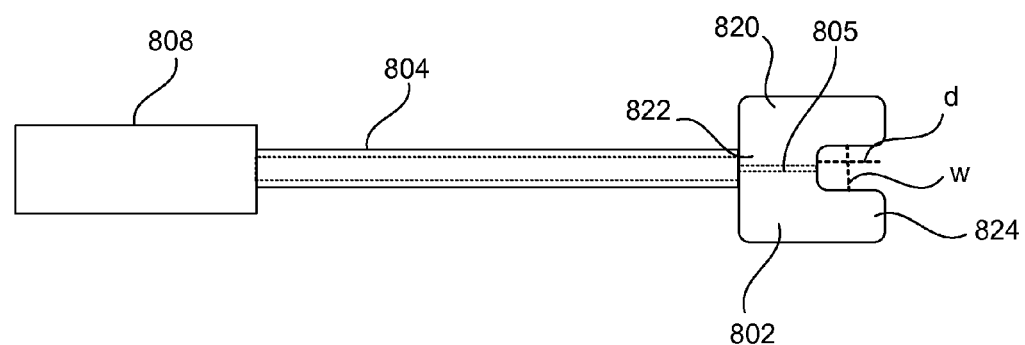
FIG. 8C illustrates a bottom view of the insertion member according to an embodiment.
Figure 8D:
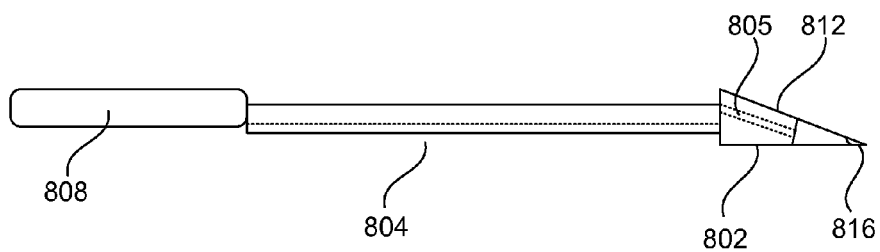
FIG. 8D illustrates a side view of the insertion member according to an embodiment.
Figure 8E:
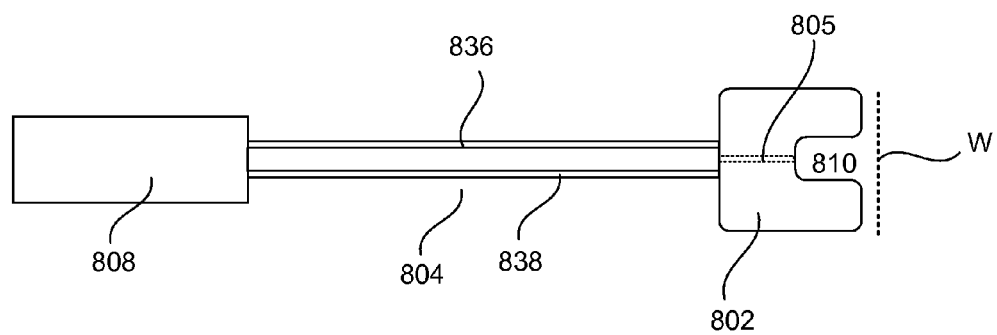
FIG. 8E illustrates a top view of the insertion member according to an embodiment.

FIG. 8A illustrates a perspective of the insertion member 800 according to an embodiment. FIG. 8B illustrates another perspective of the insertion member 800 according to an embodiment. FIG. 8C illustrates a bottom view of the insertion member 800 according to an embodiment. FIG. 8D illustrates a side view of the insertion member 800 according to an embodiment. FIG. 8E illustrates a top view of the insertion member 800 according to an embodiment. A description of the insertion member 800 will be described with reference to FIGS. 8A-8E.

Referring to FIGS. 8A-8E, the insertion member 800 may include a wedged-shaped portion 802, an elongated member 804, and a base 808. The wedge-shaped portion 802 may be coupled to a distal end of the elongated member 804. The base 808 may be coupled to a proximate end of the elongated member 804. The wedged-shaped portion 802 may be configured to grasp or engage a portion of bodily tissue when inserted into the body opening. In some examples, the wedged-shaped portion (802) or other types of insertions members discussed herein may be used to guide the needle towards the relevant tissue to be dissected. In one example, the wedged-shaped portion 802 may have a triangular-based shape such that a slope 812 of the wedged-shaped portion 802 may be defined by the depth (D) and the height (H) of the wedged-shaped portion 802. However, the wedged-shaped portion 802 is not limited to a geometric triangle shape, but rather may have curves to be more insertable (or more comfortable) in the body.

In one example, the wedged-shaped portion 802 may define a slot 810 that couples the portion of tissue when inserted into the body opening. In one example, the slot 810 may be considered a cutout portion of the wedged-shaped portion 802. The width (w) of the slot 810 may be less than the width (W) of the wedged-shaped portion 802, and the depth (d) of the slot 810 may be less than the depth (D) of the wedged-shaped portion 802. In one example, the slot 810 may begin at a distal edge 816 of the wedged-shaped portion 802 and extend into the wedged-shaped portion 802 until a certain depth d. In one example, the slot 810 may be rectangular in shape. However, the slot may encompass any type of shape. If the slot 810 includes a shape other than the rectangular shape, the width (w) along various portions of the slot 810 may have different values, and/or the depth (d) along various portions of may have different values. The slot 810 of the wedged-shaped portion 802 may allow a portion of the vaginal wall to be grasped, and then pulled within the slot 810. The distal edge 816 of the wedged-shaped portion 802 may be a relatively sharp, smooth, blunt, or a rounded edge.

In one example, the wedged-shaped portion 802 may define a lumen 805 extending from a first opening 814 on the proximate end of the wedged-shaped portion 802 to a second opening 815 on the distal end of the wedged-shaped portion. The lumen 805 is configured to receive the needle member. In one example, the lumen 805 of the wedged-shaped portion 802 may extend in a line that is parallel with the slope 812 of the wedged-shaped portion 802, as shown in FIG. 8D. The blunt tip of the needle member 102 may be inserted into the lumen 805 at the first opening 814 through the second opening 815. The orientation of the lumen 805 of the wedged-shaped portion 802 may ensure the proper orientation of insertion into the bodily tissue.

In one example, the elongated member 804 may be configured to engage the LOR injection assembly of FIGS. 5-7. In one example, the elongated member 804 may be a structure configured to connect the wedged-shaped portion 802 to the base 808, and moveably coupled to portions of the LOR injection assembly. The width of the elongated member 804 may be less than the width of the wedged-shaped portion 802. The elongated member 804 may be moveably coupled to the LOR injection assembly such that the needle member is positioned according to the desired angle of insertion. In this example, the needle member may be positioned through the first opening 814 and inserted through the lumen of the wedged-shaped portion 802 to/through the second opening. The angle of the lumen of the wedged-shaped portion 802 may correspond to the angle of insertion.

In one example, the elongated member 804 may include a groove 806 extending along the length of the elongated member 804. In one example, the elongated member 804 having the groove 806 may define a u-shaped elongated member or substantially u-shaped elongated member. For example, referring to FIG. 8B, the elongated member 804 may have a bottom portion 830 extending along the length of the elongated member 804 with a first edge wall 832 extending from the bottom portion 830 and a second edge wall 834 (opposite to the first edge wall 832) extending from the bottom portion 830. In one example, the bottom portion 830 may be rounded or flat. The first edge wall 832 and/or the second edge wall 834 may be curved or straight.

Referring to FIG. 8E (which illustrates the top view), the top portions of the first edge wall 832 and the second edge wall 834 may be shaped to have a greater thickness than the rest of the elongated member 804 or the top portions may be curved (bent) towards the middle of the elongated member 804. For example, this shape of the top portions may secure the LOR injection assembly to the elongated member 804 while allowing the LOR injection assembly to slidably move within the grooved-portion. For example, the groove 806 of the elongated member 804 may be configured to engage portions of the LOR injection assembly, and to permit the LOR injection assembly to move, thereby moving the needle member.

The base 808 may be any type of handle structure that permits an operator to insert the wedged-shaped portion 802 into the body opening. In one example, the base 808 may be a rectangle. However, the base 808 may encompass any type of structural configuration.

Figure 9:
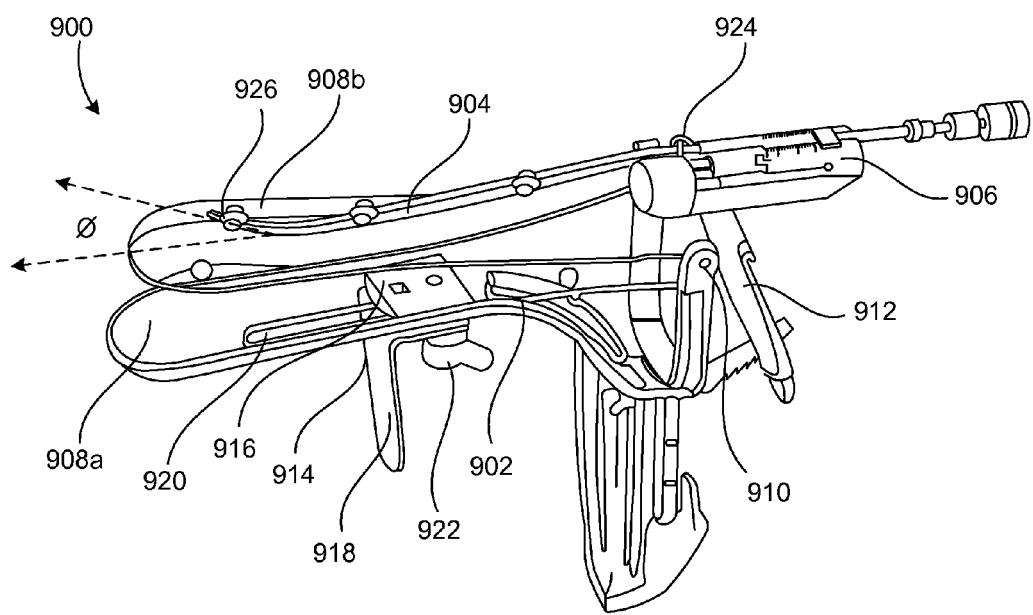
FIG. 9 illustrates an example of a medical device having an insertion member according to another embodiment.

FIG. 9 illustrates an example of a medical device 900 having an insertion member 902 according to another embodiment. The medical device 900 may be a medical device capable of being inserted into an opening of the body. In one example, the medical device 900 may be inserted in the vagina and/or the rectal canal. Further, the insertion member 902 may be coupled to a needle member and/or LOR injection assembly of the previously figures.

The insertion member 902 may include two blade members 908. For example, the blade members 908 may include a first blade member 908a positioned on the lower side of the insertion member 902, and a second blade member 908b positioned on the upper side of the insertion member 902. The first blade member 908a and the second blade member 908b may be referred to as a lower blade member 908a and an upper blade member 908b, respectively. The first blade member 908a and the second blade member 908b (hereafter collectively referred to as blade members 908a and 908b) are movable with respect to one another through a hinged portion 910 fitted at a rear portion of the insertion member 902.

In accordance with the movement of the blade members 908a and 908b, the insertion member 902 can have a range of configurations including a collapsed configuration and an expanded configuration. The expanded configuration is defined by the blade members 908a and 908b when separated from one another while the collapsed configuration is defined by the blade members 908a and 908b when contacting one another. In some embodiments, the insertion member 902 can be a speculum. In some embodiments, the speculum can be a vaginal speculum configured for vaginal inspection/examination.

The insertion member 902 can further include a clamp 912 for allowing movement of the blade members 908a and 908b, thereby changing their configurations from a collapsed to an expanded one and vice versa. Additionally, an operator may set the distance between the blade members 908a and 908b at an intermediate position, which is between the completely collapsed and completely expanded configuration depending on the surgical and/or examination requirements. In some embodiments, the second blade member 908b is movable to cause a relative movement with respect to the first blade member 908a based on an adjustment through a clamp 912. In some other embodiments, the first blade member 908a member is movable to cause a relative movement with respect to the second blade member 908b based on an adjustment through the clamp 912. In still other embodiments, both blade members 908a and 908b are movable with respect to one another to cause a relative movement. Thus, the operator can adjust the distance between the distal ends of the blade members 908a and 908b based on the surgical requirements.

Also, the insertion member 902 may include a lock assembly 914 configured to limit and/or make adjustments to the depth of insertion of the insertion member 902 in the patient's body opening. Therefore, by adjusting the lock assembly 914, the insertion member 902 enters into the body opening only to the desired depth. The lock assembly includes an upper portion 916 and a lower portion 918. The lock assembly 914 may be fitted to the first blade member 908a of the insertion member 902. In some embodiments, an opening 920 along a surface of the lower blade member 908a may be provided to securely fix the lock assembly 914 fixedly. For example, the upper portion 916 and the lower portion 918 may engage the first blade member 908a via the opening 920. In other words, the opening 920 may be configured to receive the lock assembly 914. The lower portion 918 can be moved from one position to another through a knob 922 such that this movement adjusts the depth of insertion of the insertion member 902 within the vagina or other body openings. The lower portion 918 limits insertion of the insertion member 902 because it touches the external body of the patient and does not allow further insertion.

The needle member 904 may be moveably coupled to the insertion member 902 and configured to be inserted into one or more tissue layers as discussed above. In this embodiment, the needle member 904 may be any of the needle members described with respect to the previous figures. For example, the needle member 904 may include a blunt tip, and a lumen extending to an opening on a distal end portion of the needle member 904. In addition, the LOR injection assembly including the needle member 904 of the previous figures may be coupled to the insertion member 902. In one example, the needle member 904 and/or the LOR injection assembly may be coupled to the second blade member 908b of the insertion member 902 through a set of brackets at certain positions or a projection-groove configuration. However, irrespective of the type of coupling, the needle member 904 and/or the LOR injection assembly having the needle member may be moveable with respect to the insertion member 902.

In some embodiments, the length of the needle member 904 or the LOR injection assembly having the needle member may extend along and is positioned on the second blade member 908b. The distal end portion 926 of the needle member 904 may be exposed through an opening on the second blade member 908b such that the needle member 904 protrudes upward the second blade member 908b at the distal end portion 926. In some embodiments, the needle member 904 is curved to a defined length at its distal end portion 926. The curved portion of the needle member 904 makes an angle $\phi$ with respect to a distal end portion of the second blade member 908b. In other embodiments, the coupling of the needle member 904 to the insertion member 902 may provide the insertion angle. Also, the coupling of the LOR injection assembly to the second blade member 908b may define the angle $\phi$, which provides the insertion angle as discussed above.

In some embodiments, an adjustment member 906 is coupled to a proximal end portion 924 of the needle member 904 and configured to limit advancement of the needle member 904 within the tissue layer to a predetermined depth. In other embodiments, the adjustment member 906 is omitted since the depth of needle insertion may be controlled by the blunt tip of the needle member 904 and/or the LOR injection assembly. Also, the needle member 904 may be coupled to one or more receptacles storing dissection fluid, and/or any other type of fluid used for hydrodissection. The receptacle may be any of the previous described receptacles. As such, upon the blunt tip of the needle member 904 entering the space, the dissection fluid may be injected from the one or more receptacles through the needle member 904 in a manner described above.

Figure 10A:
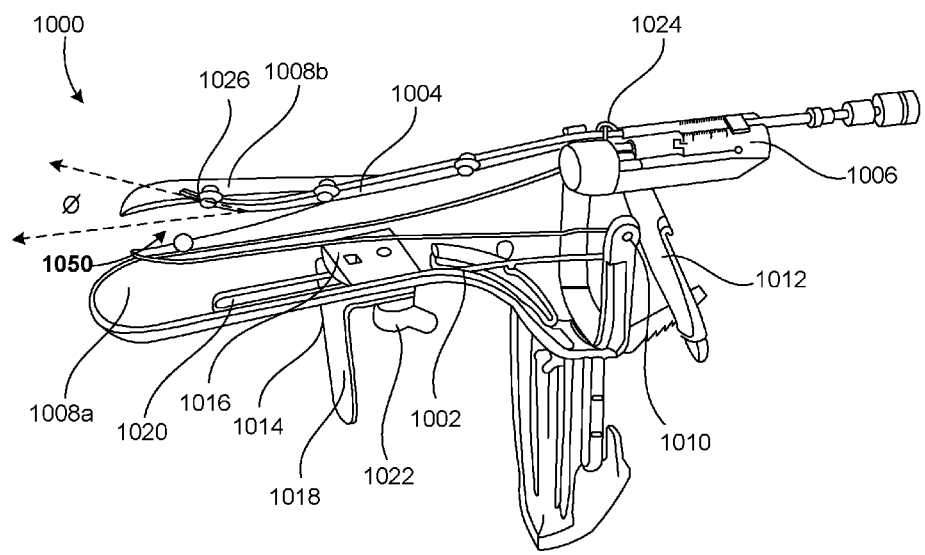
FIG. 10A illustrates an example of a medical device including an insertion member according to another embodiment.

FIG. 10A illustrates an example of a medical device 1000 including an insertion member 1002 according to another embodiment. The medical device 1000 may be a medical device capable of being inserted into an opening of the body. In one example, the medical device 1000 may be inserted in the vagina and/or the rectal canal. Further, the insertion member 1002 may be coupled to a needle member 1004 and/or the LOR injection assembly having the needle member 1004 of the previous figures.

The medical device 1000 of FIG. 10A is substantially similar to the medical device 900 of FIG. 9, and therefore, the details not pertinent to a discussion of the differences will be omitted for the sake of brevity. For example, similar to FIG. 9, the medical device 1000 may include the needle member 1004 (which may be any of the previously described needle members) having a distal end portion 1026 and a proximate end portion 1024, an insertion member 1002, and one or more receptacles (not shown) storing dissection fluid. The insertion member 1002 may include a first blade member 1008a, a second blade member 1008b, an opening 1020, a lock assembly 1014 having an upper portion 1016 and a lower portion 1018, a knob 1022, a hinged portion 1010, an adjustment member 1006, and a clamp 1012. These components are the same as previously described with reference to FIG. 9 with the exception of the second blade member 1008b.

Figure 10B:
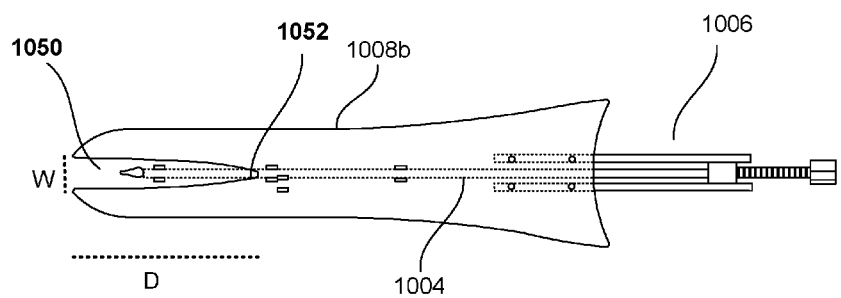
FIG. 10B illustrates the second blade member of FIG. 10A according to an embodiment.

In this example, the second blade member 1008b may include a slot 1050. For example, the slot 1050 may be cutout portion of the second blade member 1008b to facilitate the separation of the paravaginal fascia from the deeper paravesical or pararectal fascia layers. For example, the slot 1050 may allow folding of the vaginal wall before the needle member 1004 is advanced into the tissue. FIG. 10B illustrates the configuration of the second blade member 1008b having the slot 1050 in further detail.

FIG. 10B illustrates the second blade member 1008b of FIG. 10A according to an embodiment. For example, the slot 1050 may begin at the distal edge of the second blade member 1008b and extend to a position 1052 on the second blade member 1008b. In one example, the position 1052 may be disposed on the longitudinal axis of the second blade member 1008b. The slot 1050 may have a certain width (W) at the distal edge of the upper blade member 1008b. As the depth (D) of the slot 1050 increases, the width (W) of the slot 1050 decreases at various portions until reaching the position 1052. In one embodiment, the slot 1050 may be positioned in the center of second blade member 1008b along its longitudinal axis, where one end of the slot 1050 is disposed at the position 1052 which is located on the longitudinal axis.

Figure 11:
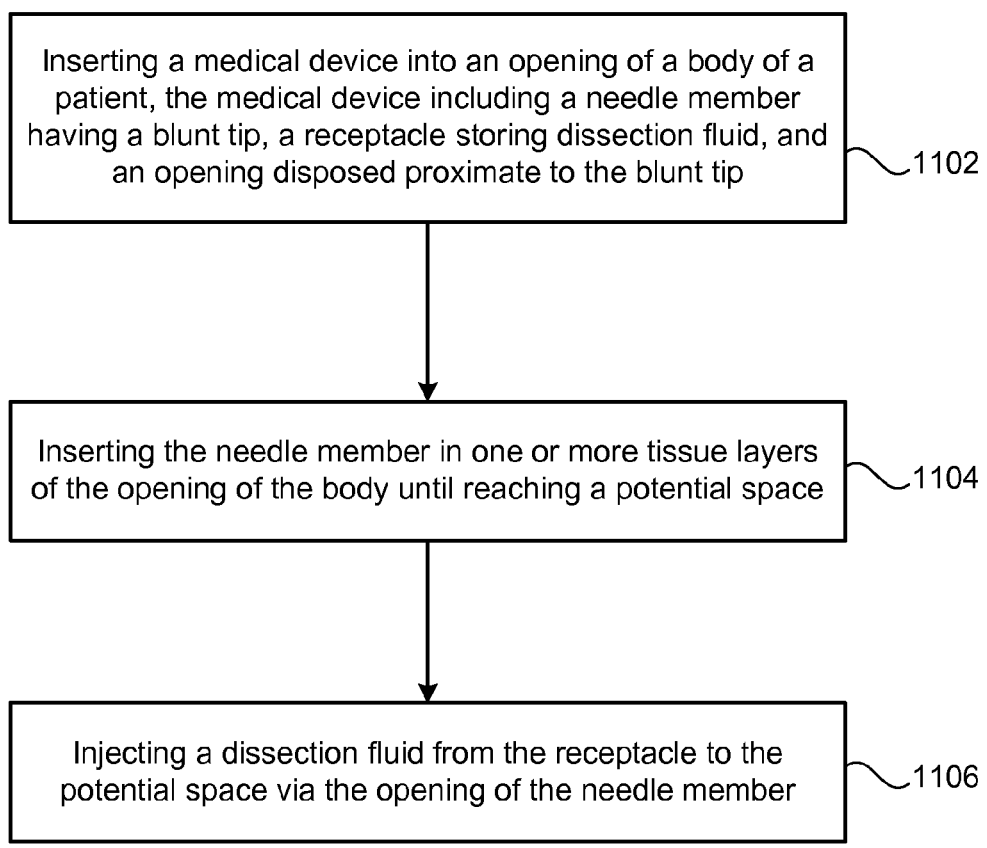
FIG. 11 illustrates a method for preparing a body of a patient for an implant according to an embodiment.

FIG. 11 is a flow chart for a method 1100 for creating space between tissue layers in the body of the patient according to an embodiment.

In step 1101, a medical device may be inserted into an opening of a patient, where the medical device may include an insertion member, a receptacle, and a needle member having a blunt tip and an opening disposed proximate to the blunt tip. For example, an operator may move the insertion member (e.g., any of the insertion members discussed with reference to the figures) into the opening of the patient. In one example, the opening may be a vagina or anal canal. With respect to FIGS. 8A-8E, as the insertion member 800 is inserted into the vagina or anal canal, the slot 810 of the wedged-shaped portion 802 may be configured to grasp a portion of the vaginal wall, and then pulled within the slot 810. The slot 810 of the wedged-shaped portion 802 may push away deeper organ layers and assist in the creation of a distraction force to facilitate the insertion of the needle member and subsequent injection. With respect to FIG. 9, the insertion member 902 may be inserted into the vagina or the anal canal. For example, the first blade member 908a and the second blade member 908b may be in a closed position, and after the insertion member 902 is inserted into the vagina, an operator may open the insertion member 902 to the opening position (e.g., the second blade member 908b being placed away from the first blade member 908a).

With respect to FIG. 10, the insertion member 1002 may be inserted into the vagina in a similar operation. However, the slot 1050 may be configured to grasp the vagina wall when configured in the open position. For example, the slot 1050 may be cutout portion of the second blade member 1008b to facilitate the separation of the paravaginal fascia from the deeper paravesical or pararectal fascia layers. For example, the slot 1050 may allow folding of the vaginal wall before the needle member 1004 is advanced into the tissue. When the insertion member 1002 is opened, the expansion of the blade members 1008 may create a counter force that would push the deeper organ layers away and help create a distraction force to facilitate the insertion of the needle member and subsequent injection.

In step 1104, the needle member may be inserted into one or more tissue layers of the opening of the body until reaching a space. For example, as explained above, the needle member, such as the needle member 102 or 202, may be moveably coupled to the insertion member. For example, the needle member may be moveably coupled to the insertion member to ensure that the needle member is properly oriented in regards to having the convex side of the needle member facing away from the vaginal lumen and angled appropriately to ensure a long needle path that would dampen needle tip movements in the Z-axis (perpendicular to the plane of the vagina).

In one example, the needle member may be initially coupled to the insertion member such that the needle member is in a refracted position. Once the insertion member is inserted into its desired location within the body opening, the operator may move the needle member from the retracted position to pierce one or more tissue layers until reaching its desired depth.

In step 1106, a dissection fluid may be injected from the receptacle to the space via the opening of the needle. For example, the needle member may be inserted into the body such that the operator may feel a loss of resistance when the blunt tip penetrates a certain tissue layer (e.g., the paravaginal fascia) (thereby reaching its desired location), which, if inserted further into the body, the blunt tip may push the deeper tissues away (as opposed to piercing them), thereby reducing the risk of the needle member 102 of entering unwanted tissue areas. In this manner, the depth of insertion may be controlled based on the structure of the needle member.

It is noted that the term space may refer to any area between tissue layers. For example, before the operator makes an incision into tissue layers in a body opening or inserting a medical implant, the operator may want to separate some tissue layers from another other tissue layers, thereby creating a space. The space may be created in order to fit a mesh implant and/or separate tissue layers which should not be pierced. In one example, the operator may insert the needle member in the body opening through one or more tissue layers until reaching the space, and then injecting dissection fluid through the needle member into the space in order to create an actual space. This process may be referred to hydrodissection. In one example, the space may be the VVS and/or the RVS. However, the embodiments encompass any types of possible areas between tissue layers.

In one embodiment, the size of the receptacle 106 may be designed such that the dissection fluid may be injected into the space to fully develop the VVS and/or the RVS without replacing the receptacle 106 with another receptacle 106. For example, smaller-type syringes may typically hold 5 cc of fluid. Larger-type syringes may typically hold 20 or 30 cc of fluid. However, the volume of fluid used for vaginal hydrodissection may be over 100 cc of fluid. As such, for smaller-type syringes and larger-type syringes, syringe exchanges may be required to develop the appropriate amount of fluid to fully develop the space. However, the needle member 102 in a 3-5 mm thick vaginal wall can easily slip out of place during syringe exchanges. Therefore, in one embodiment, the receptacle 106 may be configured to hold 100 cc to 200 cc of dissection fluid in order to avoid syringe exchanges.

In one example, the receptacle 106 maybe a pressurized reservoir of dissection fluid. In this example, the receptacle 106 may be a fluid chamber having pressurized dissection fluid. The dissection fluid may be pressurized to a certain level such that when a drop of pressure is sensed (e.g., when the needle member enters the space), the dissection fluid may be released from the fluid chamber to the space via the opening of the needle member.

In another example, the receptacle 106 may be a loss of resistance (LOR) receptacle such as a syringe, for example. In one example, the LOR receptacle may be a spring-loaded device. For example, the LOR receptacle 106 may include a compression spring, barrel, and plunger. In this example, the dissection fluid drawn up into the receptacle 106 may empty only when the needle member 102 enters a space with a relatively low tissue pressure, e.g., less than the spring constant associated with the compression spring. In this manner, the dissection fluid is automatically discharged from the LOR receptacle 106 when the LOR receptacle 106 senses that the tissue pressure is lower than the spring constant.

In some embodiments, the needle member may be part of another assembly such as an injection assembly such as the LOR injection assembly as described with reference to FIGS. 5-7. The injection assembly may include at least a portion of the needle member. Also, the injection assembly may include a pressure sensor that is configured to sense the pressure of the blunt tip of the needle member as it engages with the various bodily tissues, and an injection member that is configured to inject the dissection fluid through the lumen of the needle member into the desired location when the sensed pressure decreases below a certain pressure level. In one example, for vaginal tissue dissection, the blunt tip and the opening of the needle member may be inserted into the VVS or the RVS. As the blunt tip of the needle member is penetrating the tissue layers before reaching the VVS or the RVS, the pressure sensor may sense that the pressure is increasing, however, when the blunt tip of the needle member reaches the VVS or the RVS, the pressure may decrease (e.g., the operator may hear or feel a "pop," followed by a loss of resistance). As such, in one example, when the pressure decreases below the pressure level, the injection member may automatically inject the dissection fluid into the VVS or RVS via the needle member.

In some embodiments, a medical device may include an insertion member configured to be inserted into a body opening, and a needle member, movably coupled to the insertion member, configured to be inserted into the body opening and body tissue comprising a plurality of tissue layers. The needle member may include a lumen configured to transfer dissection fluid, a blunt tip located on a distal end of the needle member, and an opening disposed proximate to the blunt tip that is configured to discharge the dissection fluid into a space between the tissue layers.

In some embodiments, the opening may be a side-port. The insertion member may include a wedged-shaped portion, an elongated member having a distal end and a proximate end, and a base. The distal end of the elongated member may be coupled to the wedged-shaped portion, and the proximate end of the elongated member may be coupled to the base. The wedged-shaped portion may define a lumen configured to receive a portion of the needle number, and an angle of the lumen may facilitate alignment with an insertion angle of the needle member into one or more tissue layers. The wedged-shaped portion may define a slot configured to engage one or more tissue layers when inserted into the opening of the body. The insertion member may include a speculum. The speculum may include a first blade member, and a second blade member. The second blade member may be movable with respect to the second blade member, and the needle member may be moveably coupled to either the first blade member or the second blade member. The second blade member may include a slot portion configured to engage at least a portion of a vaginal wall before the needle member advances into one or more tissue layers of the vaginal wall. The medical device may include an injection assembly including at least a portion of the needle member. The injection assembly may be coupled to the insertion member, and the injection assembly may be configured to sense a tissue pressure as the needle member is inserted into the tissue layers. The injection assembly may be configured to inject the dissection fluid into the space when the tissue pressure drops below a pressure level. The injection assembly may include a pressurized chamber storing the dissection fluid that is injected into the space when the tissue pressure drops below the pressure level. The pressurized chamber may include a pressurized portion, a spacer, and a fluid receptacle portion, configured so that movement of the spacer indicates whether a distal end of the needle has entered the space. The space may include at least one of vesico vaginal space (VVS) and recto vaginal space (RVS).

In some embodiments, a medical device may include an injection assembly. The injection assembly may include a needle member having a blunt tip and an opening disposed proximate to the blunt tip, a first receptacle configured to store fluid, and a second receptacle configured to store fluid. In some examples, the second receptacle may store a different amount of fluid than the first receptacle. The injection assembly may further include a pressure sensor configured to sense a tissue pressure when the blunt tip is inserted into one or more tissue layers of a body, and an injection member configured to inject the fluid from the first receptacle into a space when the tissue pressure drops below a predetermined pressure level. The second receptacle may be configured to inject fluid into the space after the fluid from the first receptacle has been injected.

In some embodiments, the second receptacle may be configured to store sufficient fluid to open the space without an exchange of receptacles. The first receptacle may be configured to release the pressurized fluid into the space via the needle member when the tissue pressure drops below a predetermined pressure level. The first receptacle may include a pressurized portion, a spacer, and a fluid receptacle portion, configured so that movement of the spacer indicates whether a distal end of the needle has entered the space. The medical device may include an insertion member, movably coupled to the injection assembly, the insertion member being configured to be inserted into a vagina of a patient.

In some embodiments, a method for creating space between tissue layers in the body of a patient may include inserting a portion of a medical device into an opening of the body. The medical device may include a needle member, a receptacle storing dissection fluid, and an opening disposed proximate to the needle member. The method may further include inserting the needle member into one or more tissue layers of the opening of the body until reaching a space, and injecting a dissection fluid from the receptacle to the space via the opening of the needle member.

In some embodiments, the method may further include sensing a tissue pressure at a distal end of the needle member of the one or more tissue layers, and automatically injecting the dissection fluid into the space when the tissue pressure drops below a predetermined pressure level. The method may further include performing a hydrodissection on the space without exchanging receptacles.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device comprising:
an insertion member configured to be inserted into a body opening;
a needle member, movably coupled to the insertion member, configured to be inserted into the body opening and body tissue comprising a plurality of tissue layers, the needle member including a lumen configured to transfer dissection fluid, a blunt tip located on a distal end of the needle member, and an opening disposed proximate to the blunt tip that is configured to discharge the dissection fluid into a space between the tissue layers; and
an injection assembly coupled to the needle member, the injection assembly including a pressure sensor configured to sense tissue pressure, the pressure sensor configured to provide visual feedback to an operator when the sensed tissue pressure drops below a pressure level, the visual feedback indicating that a distal end of the needle member has entered the space.

2. The medical device of claim 1, wherein the opening is a side-port.

3. The medical device of claim 1, wherein the insertion member includes a wedged-shaped portion, an elongated member having a distal end and a proximate end, and a base, the distal end of the elongated member being coupled to the wedged-shaped portion, the proximate end of the elongated member being coupled to the base.

4. The medical device of claim 3, wherein the wedged-shaped portion defines a lumen configured to receive a portion of the needle number, and an angle of the lumen facilitates alignment with an insertion angle of the needle member into one or more tissue layers.

5. The medical device of claim 3, wherein the wedged-shaped portion defines a slot configured to engage one or more tissue layers when inserted into the body opening.

6. The medical device of claim 1, wherein the insertion member includes a speculum.

7. The medical device of claim 6, wherein the speculum includes a first blade member, and a second blade member, the second blade member being movable with respect to the first blade member, the needle member being moveably coupled to either the first blade member or the second blade member.

8. The medical device of claim 7, wherein the second blade member includes a slot portion configured to engage at least a portion of a vaginal wall before the needle member advances into one or more tissue layers of the vaginal wall.

9. The medical device of claim 1, wherein the injection assembly is configured to automatically inject the dissection fluid into the space when the tissue pressure drops below the pressure level.

10. The medical device of claim 1, wherein the injection assembly includes a pressurized chamber storing the dissection fluid that is injected into the space when the tissue pressure drops below the pressure level.

11. The medical device of claim 10, wherein the pressurized chamber includes a pressurized portion, a spacer, and a fluid receptacle portion, configured so that movement of the spacer indicates whether the distal end of the needle has entered the space.

12. The medical device of claim 1, wherein the space includes at least one of vesico vaginal space (VVS) and recto vaginal space (RVS).

13. The medical device of claim 1, wherein the injection assembly is configured to place a hold on movement of the needle member when the distal end of the needle member has entered the space, and the injection assembly is configured to release the hold to permit movement of the needle member upon injection of the dissection fluid into the space.

14. A medical device comprising:
an insertion member configured to be inserted into a body opening, insertion member including a wedged-shaped portion having a slot configured to receive body tissue, the wedged-shaped portion defining an internal lumen that extends to the slot; and
a needle member configured to be inserted through the internal lumen of the wedged-shaped portion and into the body tissue, the needle member including a lumen configured to transfer dissection fluid, a blunt tip located on a distal end of the needle member, and an opening disposed proximate to the blunt tip that is configured to discharge the dissection fluid into a space between tissue layers of the body tissue.

15. The medical device of claim 14, wherein the wedged-shaped portion has a linear slope portion, the linear slope portion having a slope defined by a depth and height of the wedged-shaped portion, the internal lumen being disposed parallel to the slope of the linear slop portion.

16. The medical device of claim 14, wherein the insertion member includes an elongated member extending proximally from the wedged-shaped portion, the internal lumen being disposed at a non-zero angle with respect to a longitudinal axis of the elongated member.

17. The medical device of claim 14, further comprising:
an injection assembly coupled to the needle member, the injection assembly including a pressure sensor configured to sense tissue pressure, the pressure sensor configured to provide visual feedback to an operator when the sensed tissue pressure drops below a pressure level, the visual feedback indicating that a distal end of the needle member has entered the space.

18. The medical device of claim 17, wherein the injection assembly includes a pressurized chamber storing the dissection fluid that is injected into the space when the tissue pressure drops below the pressure level, the pressurized chamber including a pressurized portion, a spacer, and a fluid receptacle portion, configured so that movement of the spacer indicates whether the distal end of the needle has entered the space.

* * * * *